US011426469B2

(12) United States Patent
Gao et al.

(10) Patent No.: US 11,426,469 B2
(45) Date of Patent: Aug. 30, 2022

(54) PROSTATE-TARGETING ADENO-ASSOCIATED VIRUS SEROTYPE VECTORS

(71) Applicant: University of Massachusetts, Boston, MA (US)

(72) Inventors: Guangping Gao, Westborough, MA (US); Jianzhong Ai, Worcester, MA (US); Hong Li, Worcester, MA (US); Qiang Wei, Worcester, MA (US)

(73) Assignee: University of Massachusetts, Boston, MA (US)

( * ) Notice: Subject to any disclaimer, the term of this patent is extended or adjusted under 35 U.S.C. 154(b) by 588 days.

(21) Appl. No.: 15/769,953

(22) PCT Filed: Oct. 21, 2016

(86) PCT No.: PCT/US2016/058185
§ 371 (c)(1),
(2) Date: Apr. 20, 2018

(87) PCT Pub. No.: WO2017/070516
PCT Pub. Date: Apr. 27, 2017

(65) Prior Publication Data
US 2018/0311380 A1    Nov. 1, 2018

Related U.S. Application Data

(60) Provisional application No. 62/322,285, filed on Apr. 14, 2016, provisional application No. 62/245,027, filed on Oct. 22, 2015.

(51) Int. Cl.
| *A61K 48/00* | (2006.01) |
| *C12N 15/86* | (2006.01) |
| *C12N 5/10* | (2006.01) |
| *C07K 14/075* | (2006.01) |
| *C07K 14/005* | (2006.01) |
| *A61K 9/00* | (2006.01) |
| *A61K 38/17* | (2006.01) |
| *A61P 35/00* | (2006.01) |
| *C07K 14/47* | (2006.01) |

(52) U.S. Cl.
CPC ........ *A61K 48/0058* (2013.01); *A61K 9/0019* (2013.01); *A61K 9/0034* (2013.01); *A61K 38/1709* (2013.01); *A61K 48/00* (2013.01); *A61P 35/00* (2018.01); *C07K 14/005* (2013.01); *C07K 14/075* (2013.01); *C12N 5/10* (2013.01); *C12N 15/86* (2013.01); *C07K 14/47* (2013.01); *C12N 2750/10041* (2013.01); *C12N 2750/14121* (2013.01); *C12N 2750/14122* (2013.01); *C12N 2750/14143* (2013.01); *C12N 2750/14145* (2013.01); *C12N 2840/007* (2013.01)

(58) Field of Classification Search
None
See application file for complete search history.

(56) References Cited

U.S. PATENT DOCUMENTS

| 5,478,745 | A | 12/1995 | Samulski et al. |
| 5,871,982 | A | 2/1999 | Wilson et al. |
| 6,156,303 | A | 12/2000 | Russell et al. |
| 6,251,677 | B1 | 6/2001 | Wilson et al. |
| 6,485,966 | B2 | 11/2002 | Gao et al. |
| 6,498,244 | B1 | 12/2002 | Patel et al. |
| 6,544,786 | B1 | 4/2003 | Xiao et al. |
| 6,953,690 | B1 | 10/2005 | Gao et al. |
| 6,962,815 | B2 | 11/2005 | Bartlett |
| 7,022,519 | B2 | 4/2006 | Gao et al. |
| 7,198,951 | B2 | 4/2007 | Gao et al. |
| 7,235,393 | B2 | 6/2007 | Gao et al. |
| 7,267,978 | B1 * | 9/2007 | Carey ............... A61K 48/00 435/320.1 |
| 7,282,199 | B2 | 10/2007 | Gao et al. |
| 7,427,396 | B2 | 9/2008 | Arbetman et al. |
| 7,456,015 | B2 | 11/2008 | Bohn et al. |
| 7,906,111 | B2 | 3/2011 | Wilson et al. |
| 8,222,221 | B2 | 7/2012 | Corey et al. |
| 8,524,446 | B2 | 9/2013 | Gao et al. |
| 8,734,809 | B2 | 5/2014 | Gao et al. |
| 9,249,424 | B2 | 2/2016 | Wolf et al. |
| 9,701,984 | B2 | 7/2017 | Gao et al. |
| 2001/0016355 | A1 | 8/2001 | Samulski et al. |
| 2002/0164783 | A1 | 11/2002 | Feldhaus |
| 2002/0192823 | A1 | 12/2002 | Bartlett |
| 2003/0103939 | A1 | 6/2003 | Engelhardt et al. |

(Continued)

FOREIGN PATENT DOCUMENTS

| EP | 2261242 A1 | 12/2010 |
| EP | 2468891 A2 | 6/2012 |

(Continued)

OTHER PUBLICATIONS

Genbank Y18065 to AAV5 Cap protein, 1999. 3 pages.*

(Continued)

*Primary Examiner* — James D Schultz
*Assistant Examiner* — Kimberly A Aron
(74) *Attorney, Agent, or Firm* — Wolf, Greenfield & Sacks, P.C.

(57) ABSTRACT

The disclosure relates to compositions and methods for rAAV-mediated delivery of a transgene to a subject. In some embodiments, the rAAV transduces the prostate tissue of a subject. In some embodiments, the methods are useful for treatment of prostate disease (e.g., prostatitis, BPH, prostate cancer).

20 Claims, 20 Drawing Sheets
Specification includes a Sequence Listing.

(56) References Cited

U.S. PATENT DOCUMENTS

| | | |
|---|---|---|
| 2003/0110526 A1 | 6/2003 | Brown et al. |
| 2003/0138772 A1 | 7/2003 | Gao et al. |
| 2003/0228282 A1 | 12/2003 | Gao et al. |
| 2004/0101514 A1 | 5/2004 | Liu et al. |
| 2005/0014262 A1 | 1/2005 | Gao et al. |
| 2005/0164970 A1* | 7/2005 | Li .................. C12N 15/1138 536/23.1 |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0239968 A1* | 10/2006 | Arap .................. C07K 16/30 424/93.2 |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2008/0075737 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0227533 A1* | 9/2009 | Bader .................. A61P 31/10 514/44 R |
| 2010/0104561 A1 | 4/2010 | Zhong et al. |
| 2010/0227909 A1 | 9/2010 | Cleary et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| JP | 2008-538286 | 10/2008 |
| WO | WO 2003/042397 | 5/2003 |
| WO | WO 2004/108922 A2 | 12/2004 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2008/150897 A2 | 12/2008 |
| WO | WO 2008/154333 A2 | 12/2008 |
| WO | WO 2009/43936 | 4/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Genbank AF513851 to AAV7 Cap protein, 2002. 3 pages.*
Genbank AF513852 AAV8 Cap protein, 2002. 3 pages.*
Genbank AY243015 to AAVrh10 Cap protein, 2003. 2 pages.*
Isayeva et. al. Effects of Sustained Antiangiogenic Therapy in Multistage Prostate Cancer in TRAMP Model, as evidenced by Grimm et al. Helper-free, Optically Controllable, and Two-Plasmid-Based Production of Adeno-Associated Virus Vectors of Serotypes 1 to 6. Molecular Therapy, 2003. 7(6):839-850.*
Grimm et al. Helper-free, Optically Controllable, and Two-Plasmid-Based Production of Adeno-Associated Virus Vectors of Serotypes 1 to 6. Molecular Therapy, 2003. 7(6):839-850.*
Rutledge et al. Infectious Clones and Vectors Derived from Adeno-Associated Virus (AAV) Serotypes Other than AAV Type 2. Journal of Virology, 1998. 309-319.*
Hacker et al. Adeno-associated Virus Serotypes 1 to 5 Mediated Tumor Cell Directed Gene Transfer and Improvement of Transduction Efficiency. The Journal of Gene Medicine, 2005. 7: 1429-1438.*
Lisowski et al. Adeno-Associated Virus Serotypes for Gene Therapeutics. Current Opinion in Pharmacology, Oct. 2015. 24:59-67.*
Van Vliet et al. (2008) The Role of the Adeno-Associated Virus Capsid in Gene Transfer. In: Jain K.K. (eds) Drug Delivery Systems. Methods in Molecular Biology™, vol. 437. 51-91.*
Messina, et al. Adeno-Associated Viral Vectors Based on Serotype 3b Use Components of the Fibroblast Growth Factor Receptor Signaling Complex for Efficient Transduction. Human Gene Therapy, 2012. 23(10): 1031-1042.*
Adachi et al., Drawing a high-resolution functional map of adeno-associated virus capsid by massively parallel sequencing. Nat Commun. 2014;5:3075. doi: 10.1038/ncomms4075.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Arbuthnot et al., Hepatic delivery of RNA interference activators for therapeutic application. Curr Gene Ther. Apr. 2009;9(2):91-103.
Asokan et al., The AAV vector toolkit: poised at the clinical crossroads. Mol Ther. Apr. 2012;20(4):699-708. doi: 10.1038/mt.2011.287. Epub Jan. 24, 2012.

(56) References Cited

OTHER PUBLICATIONS

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Bals et al., Transduction of well-differentiated airway epithelium by recombinant adeno-associated virus is limited by vector entry. J Virol. Jul. 1999;73(7):6085-8.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.

Choudhury et al., Identification of Novel vectors capable of CNS transduction in adult mice after single round selection using DNA shuffled AAV capsid library. Mol Ther. May 1, 2013;21(1):S1/.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Conlon et al., Ribozyme Approaches towards Down-Regulation of Pi*Z Mutant Human a-1 Anti-Trypsin. Mol. Therapy. 2004;9:S333. Abstract 875.

Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.

Cruz et al., The promise of gene therapy for the treatment of alpha-1 antitrypsin deficiency. Pharmacogenomics. Sep. 2007;8(9):1191-8.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Daya et al., Gene therapy using adeno-associated virus vectors. Clin Microbiol Rev. Oct. 2008;21(4):583-93. doi: 10.1128/CMR.00008-08.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Ehlert et al., Cellular toxicity following application of adeno-associated viral vector-mediated RNA interference in the nervous system. BMC Neurosci. Feb. 18, 2010;11:20.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Foust et al., Intravascular AAV9 preferentially targets neonatal-neurons and adult-astrocytes. Nature Biotechnology, 27; 59-65 2009.

Foust et al., Over the barrier and through the blood: to CNS delivery we go. Cell Cycle. Dec. 15, 2009;8(24):4017-8.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Fu et al., Self-complementary adeno-associated virus serotype 2 vector: global distribution and broad dispersion of AAV-mediated transgene expression in mouse brain. Mol Ther. Dec. 2003;8(6):911-7.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.

Gao et al., Biology of AAV serotype vectors in liver-directed gene transfer to nonhuman primates. Mol Ther. Jan. 2006;13(1):77-87. Epub Oct. 10, 2005.

Gao et al., Clades of Adeno-associated viruses are widely disseminated in human tissues. J Virol. Jun. 2004;78(12):6381-8.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., RAAV-mediated targeting in adult mice and its potential in generating animal models of tissue-specific somatic transgenics or knock down. Molecular Therapy. May 2008;16(1):S118-S119. Abstract 316.

(56) References Cited

OTHER PUBLICATIONS

Genbank Submission; Accession No. ADZ26851; Wilson et al.; Jun. 30, 2005.
Genbank Submission; Accession No. AF028705.1; Rutledge et al.; Jan. 12, 1998.
Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.
Genbank Submission; NCBI, Accession No. ACB55310; Vandenberghe et al.; Jul. 31, 2008.
Genbank Submission; NCBI, Accession No. AY530579.10; 2004.
Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Iida et al., Systemic Delivery of Tyrosine-Mutant AAV Vectors Results in Robust Transduction of Neurons in Adult Mice. BioMed Res Int. 2013;2013.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.
Lebherz et al., Gene therapy with novel adeno-associated virus vectors substantially diminishes atherosclerosis in a murine model of familial hypercholesterolemia. J Gene Med. Jun. 2004;6(6):663-72.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Ex vivo transduction and transplantation of bone marrow cells for liver gene delivery of alpha1-antitrypsin. Mol Ther. Aug. 2010;18(8):1553-8. Epub Jun. 15, 2010.
Li et al., Protein trans-splicing as a means for viral vector-mediated in vivo gene therapy. Hum Gene Ther. Sep. 2008;19(9):958-64. doi: 10.1089/hum.2008.009.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
Mccarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
NCBI BLAST Protein Sequence. RID-09JSKF33114. Alignment of Seq ID Nos. 87, 179. 2016.
O'Reilly et al., RNA interference-mediated suppression and replacement of human rhodopsin in vivo. Am J Hum Genet. Jul. 2007;81(1):127-35. Epub May 23, 2007.

(56) References Cited

OTHER PUBLICATIONS

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Tarasov et al., Differential Regulation of microRNAs by p53 Revealed by Massively Parallel Sequencing: miR-34a is a p53 Target That Induces Apoptosis and G1-arrest. Cell Cycle. Jul. 1, 2007;6(13):1586-93. Epub May 11, 2007.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding and transduction by adeno-associated virus types 1 and 6. J Virol. Sep. 2006;80(18):9093-103.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Xu et al., Delivery of MDR1 small interfering RNA by self-complementary recombinant adeno-associated virus vector. Mol Ther. Apr. 2005;11(4):523-30.
Yan et al., Unique biologic properties of recombinant AAV1 transduction in polarized human airway epithelia. J Biol Chem. Oct. 6, 2006;281(40):29684-92. Epub Aug. 9, 2006.
Zabner et al., Adeno-associated virus type 5 (AAV5) but not AAV2 binds to the apical surfaces of airway epithelia and facilitates gene transfer. J Virol. Apr. 2000;74(8):3852-8.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.

(56) References Cited

OTHER PUBLICATIONS

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

Extended European Search Report for Application No. 16858324.3, dated May 15, 2019.

Dash et al., Developing an effective gene therapy for prostate cancer: New technologies with potential to translate from the laboratory into the clinic. Discov Med. Jan. 2011;11(56):46-56.

Limberis et al., Transduction efficiencies of novel AAV vectors in mouse airway epithelium in vivo and human ciliated airway epithelium in vitro. Mol Ther. Feb. 2009;17(2):294-301. doi: 10.1038/mt.2008.261. Epub Dec. 9, 2008.

Liu et al., The microRNA miR-34a inhibits prostate cancer stem cells and metastasis by directly repressing CD44. Nat Med. Feb. 2011;17(2):211-5. doi: 10.1038/nm.2284. Epub Jan. 16, 2011.

Sayroo et al., Development of novel AAV serotype 6 based vectors with selective tropism for human cancer cells. Gene Ther. Jan. 2016;23(1):18-25. doi: 10.1038/gt.2015.89. Epub Oct. 8, 2015.

\* cited by examiner

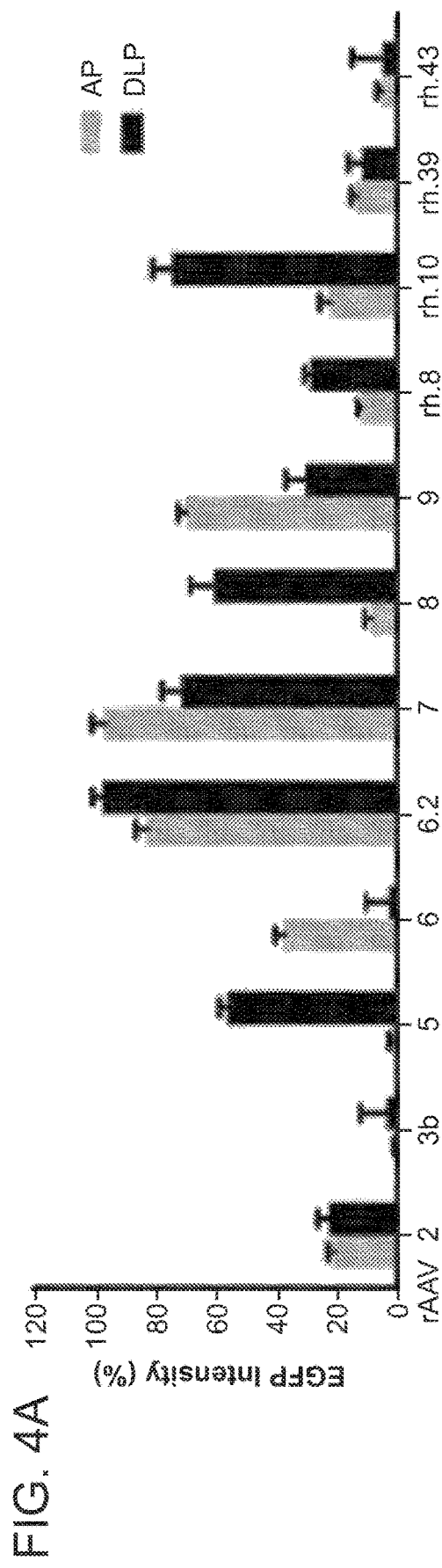
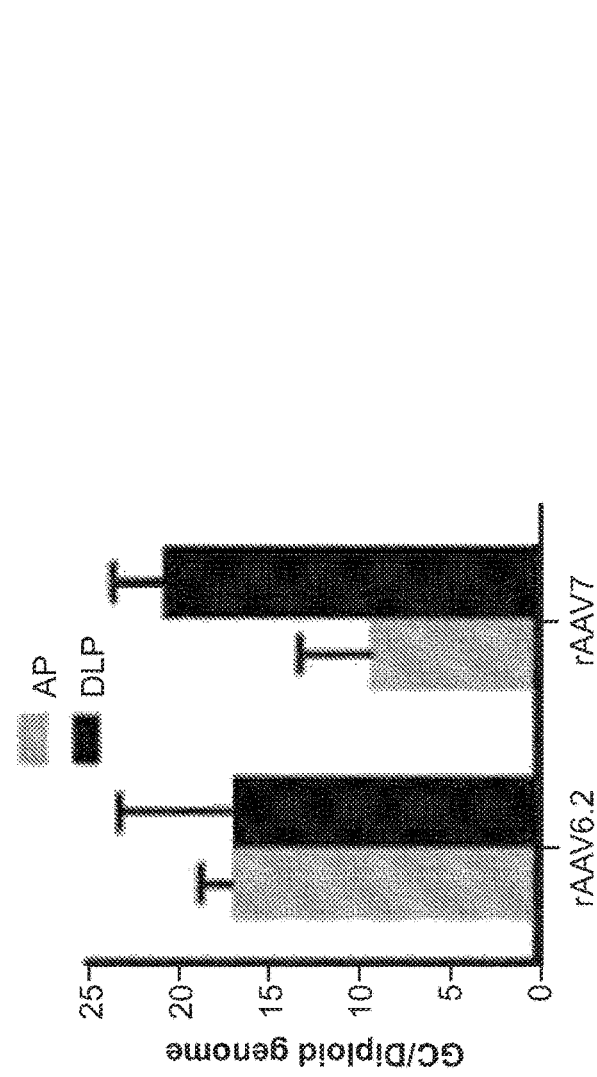
FIG. 4A
FIG. 4B

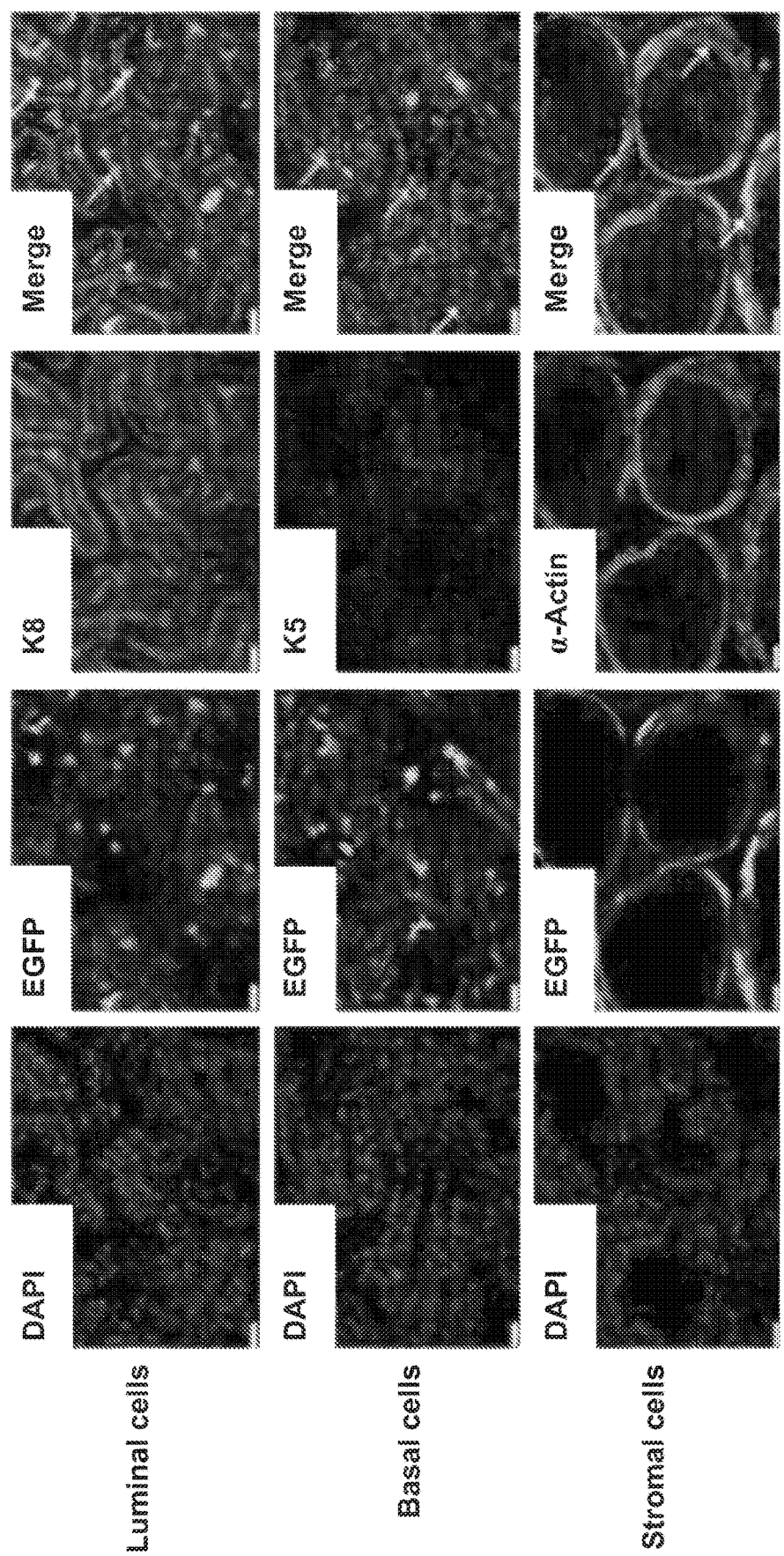

BS: Binding site
PSL: irrelevant plasmids

Wound Healing Assay

SEQUENCE LISTING

```
<160> NUMBER OF SEQ ID NOS: 16

<210> SEQ ID NO 1
<211> LENGTH: 724
<212> TYPE: PRT
<213> ORGANISM: Artificial Sequence
<220> FEATURE:
<223> OTHER INFORMATION: Synthetic Polypeptide

<400> SEQUENCE: 1

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300
```

-continued

```
Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
                340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu
```

```
<210> SEQ ID NO 2
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365
```

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 3

-continued

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
    275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
        340                 345                 350

Tyr Val Leu Gly Ser Ala His Gln Gly Cys Leu Pro Pro Phe Pro Ala
    355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Phe Gly Leu
625                 630                 635                 640

Lys His Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
    660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 737
<212> TYPE: PRT
<213> ORGANISM: Artificial Sequence
<220> FEATURE:
<223> OTHER INFORMATION: Synthetic Polypeptide

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45
```

-continued

```
Gly Tyr Lys Tyr Leu Gly Pro Phe Asn Gly Leu Asp Lys Gly Glu Pro
         50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Thr Val Ala Ala Gly Gly
            195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
450                 455                 460

Phe Tyr Gln Gly Gly Pro Ser Thr Met Ala Glu Gln Ala Lys Asn Trp
```

```
                465                 470                 475                 480
Leu Pro Gly Pro Cys Phe Arg Gln Gln Arg Val Ser Lys Thr Leu Asp
                    485                 490                 495
Gln Asn Asn Asn Ser Asn Phe Ala Trp Thr Gly Ala Thr Lys Tyr His
                500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
        530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
                565                 570                 575
Glu Tyr Gly Ile Val Ser Ser Asn Leu Gln Ala Ala Asn Thr Ala Ala
                580                 585                 590
Gln Thr Gln Val Val Asn Asn Gln Gly Ala Leu Pro Gly Met Val Trp
            595                 600                 605
Gln Asn Arg Asp Val Tyr Leu Gln Gly Pro Ile Trp Ala Lys Ile Pro
        610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Glu Val Phe Thr Pro Ala Lys Phe Ala Ser Phe Ile
                660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
        690                 695                 700
Asn Phe Glu Lys Gln Thr Gly Val Asp Phe Ala Val Asp Ser Gln Gly
705                 710                 715                 720
Val Tyr Ser Glu Pro Arg Pro Ile Gly Thr Arg Tyr Leu Thr Arg Asn
                725                 730                 735
Leu

<210> SEQ ID NO 5
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 5

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
```

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510
```

```
Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Leu Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 6
<211> LENGTH: 736
<212> TYPE: PRT
<213> ORGANISM: Artificial Sequence
<220> FEATURE:
<223> OTHER INFORMATION: Synthetic Polypeptide

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
```

```
               130                 135                 140
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560
```

Thr Asn Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 738
<212> TYPE: PRT
<213> ORGANISM: Artificial Sequence
<220> FEATURE:
<223> OTHER INFORMATION: Synthetic Polypeptide

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

```
Pro Ala Gly Pro Ser Gly Leu Gly Ser Gly Thr Met Ala Ala Gly Gly
            195                 200                 205
Gly Ala Pro Met Ala Asp Asn Asn Glu Gly Ala Asp Gly Val Gly Ser
210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Ser Thr Asn Asp
            260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
            290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
            370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
            450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
            530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Gln Asn Ala Ala
            580                 585                 590
Pro Ile Val Gly Ala Val Asn Ser Gln Gly Ala Leu Pro Gly Met Val
            595                 600                 605
```

```
Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 8
<211> LENGTH: 2172
<212> TYPE: DNA
<213> ORGANISM: Artificial Sequence
<220> FEATURE:
<223> OTHER INFORMATION: Synthetic Polynucleotide

<400> SEQUENCE: 8
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
gagaagctcg ccgacgacac atccttcggg ggaaacctcg gaaaggcagt cttttcaggcc    360 aagaaaaggg ttctcgaacc ttttggcctg gttgagagg gtgctaagac ggcccctacc     420
ggaaagcgga tagacgacca ctttccaaaa agaaagaagg cccggaccga gaggactcc     480 aagccttcca cctcgtcaga cgccgaagct ggacccagcg atcccagca gctgcaaatc      540 ccagcccaac cagcctcaag tttgggagct gatacaatgt ctgcgggagg tgcggcccca     600
ttgggcgaca taaccaagg tgccgatgga gtgggcaatg cctcgggaga ttggcattgc     660
gattccacgt ggatggggga cagagtcgtc accaagtcca cccgaacctg ggtgctgccc     720
agctacaaca accaccagta ccgagagatc aaaagcggct ccgtcgacgg aagcaacgcc     780
aacgcctact ttggatacag caccccctgg gggtactttg actttaaccg cttccacagc    840
cactggagcc cccgagactg gcaaagactc atcaacaact actggggctt cagaccccgg     900
tccctcagag tcaaaatctt caacattcaa gtcaaagagg tcacggtgca ggactccacc    960
accaccatcg ccaacaacct cacctccacc gtccaagtgt tacggacga cgactaccag    1020 ctgccctacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca agatgctgag aacgggcaac    1200
aactttgagt taacctacaa ctttgaggag gtgcccttcc actccagctt cgctcccagt    1260
cagaacctct tcaagctggc caaccgcgct ggtggaccagt acttgtaccg cttcgtgagc    1320
```

| | | |
|---|---|---|
| acaaataaca ctggcggagt ccagttcaac aagaacctgg ccgggagata cgccaacacc | 1380 |
| tacaaaaact ggttcccggg gcccatgggc cgaacccagg gctggaacct gggctccggg | 1440 |
| gtcaaccgcg ccagtgtcag cgccttcgcc acgaccaata ggatggagct cgagggcgcg | 1500 |
| agttaccagg tgcccccgca gccgaacggc atgaccaaca acctccaggg cagcaacacc | 1560 |
| tatgccctgg agaacactat gatcttcaac agccagccgg cgaacccggg caccaccgcc | 1620 |
| acgtacctcg agggcaacat gctcatcacc agcgagagcg agacgcagcc ggtgaaccgc | 1680 |
| gtggcgtaca acgtcggcgg gcagatggcc accaacaacc agagctccac cactgccccc | 1740 |
| gcgaccggca cgtacaacct ccaggaaatc gtgcccggca gcgtgtggat ggagagggac | 1800 |
| gtgtacctcc aaggacccat ctgggccaag atcccagaga cggggcgca ctttcacccc | 1860 |
| tctccggcca tgggcggatt cggactcaaa cacccaccgc ccatgatgct catcaagaac | 1920 |
| acgcctgtgc ccggaaatat caccagcttc tcggacgtgc ccgtcagcag cttcatcacc | 1980 |
| cagtacagca ccgggcaggt caccgtggag atggagtggg agctcaagaa ggaaaaactcc | 2040 |
| aagaggtgga acccagagat ccagtacaca aacaactaca acgaccccca gtttgtggac | 2100 |
| tttgccccgg acagcaccgg ggaatacaga accaccagac ctatcggaac ccgatacctt | 2160 |
| acccgacccc tt | 2172 |

<210> SEQ ID NO 9
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 9

| | | |
|---|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg gacccttcaa cggactcgac | 180 |
| aaggggagc ccgtcaacgc ggcggatgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcagtcgcca caagagccag actcctcctc gggcattggc | 480 |
| aagacaggcc agcagcccgc taaaaagaga ctcaattttg gtcagactgg cgactcagag | 540 |
| tcagtccccg acccacaacc tctcggagaa cctccagcaa ccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgaacatg gccttgccc acctataaca accacctcta caagcaaatc | 780 |
| tccagtgctt caacgggggc cagcaacgac aaccactact cggctacag cacccctggg | 840 |
| gggtattttg atttcaacag attccactgc catttctcac acgtgactg gcagcgactc | 900 |
| atcaacaaca ttggggatt ccggcccaag agactcaact tcaagctctt caacatccaa | 960 |
| gtcaaggagg tcacgacgaa tgatggcgtc acgaccatcg ctaataacct taccagcacg | 1020 |
| gttcaagtct ctcggactc ggagtaccag ttgccgtacg tcctcggctc tgcgcaccag | 1080 |
| ggctgcctcc ctccgttccc ggcggacgtg ttcatgattc cgcagtacgg ctacctaacg | 1140 |

```
ctcaacaatg gcagccaggc agtgggacgg tcatcctttt actgcctgga atatttccca   1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccgggggtc tccagctggc atgtctgttc agcccaaaaa ctggctacct   1440
ggaccctgtt accggcagca gcgcgttcct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt tctttcccat gagcggtgtc   1620 atgattttg gaaggagag cgccggagct tcaaacactg cattggacaa tgtcatgatc   1680
acagacgaag aggaaatcaa agccactaac cccgtggcca ccgaaagatt tgggactgtg   1740
gcagtcaatc tccagagcag cagcacagac cctgcgaccg gagatgtgca tgttatggga   1800
gccttacctg gaatggtgtg gcaagacaga gacgtatacc tgcagggtcc tatttgggcc   1860
aaaattcctc acacggatgg acactttcac ccgtctcctc tcatgggcgg ctttggactt   1920 aagcaccgc ctcctcagat cctcatcaaa acacgcctg ttcctgcgaa tcctccggca   1980
gagttttcgg ctacaaagtt tgcttcattc atcacccagt attccacagg acaagtgagc   2040
gtggagattg aatgggagct gcagaaagaa aacagcaaac gctggaatcc gaagtgcag   2100 tatacatcta actatgcaaa atctgccaac gttgatttca ctgtggacaa caatggactt   2160
tatactgagc ctcgccccat tggcacccgt tacctcaccc gtcccctg               2208

<210> SEQ ID NO 10
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 10
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg acccttcaa cggactcgac    180 aagggggagc ccgtcaacgc ggcggatgca gcggccctcg agcacgacaa ggcctacgac    240
cagcagctca aagcgggtga caatccgtac ctgcggtata ccacgccga cgccgagttt    300 caggagcgtc tgcaagaaga tacgtctttt ggggcaacc tcgggcgagc agtcttccag    360
gccaagaaga gggttctcga acctcttggt ctggttgagg aaggtgctaa gacggctcct    420
ggaaagaaac gtccggtaga gcagtcgcca aagagccag actcctcctc gggcattggc    480
aagacaggcc agcagcccgc taaaaagaga ctcaattttg gtcagactgg cgactcagag    540
tcagtccccg acccacaacc tctcggagaa cctccagcaa ccccgctgc tgtgggacct    600 actacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgaacatg gccttgcccc acctataaca accacctcta caagcaaatc    780
tccagtgctt caacggggc cagcaacgac aaccactact cggctacag caccccctgg    840 gggtattttg atttcaacag attccactgc catttctcac cacgtgactg gcagcgactc    900
atcaacaaca ttggggatt ccggcccaag agactcaact tcaagctctt caacatccaa    960
gtcaaggagg tcacgacgaa tgatggcgtc acgaccatcg ctaataacct taccagcacg   1020
```

```
gttcaagtct tctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg cagccaggc agtgggacgg tcatccttt actgcctgga atatttccca    1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccgggggtc tccagctggc atgtctgttc agcccaaaaa ctggctacct   1440
ggaccctgtt accggcagca gcgcgtttct aaaacaaaaa cagacaacaa caacagcaac   1500
tttacctgga ctggtgcttc aaaatataac cttaatgggc gtgaatctat aatcaaccct   1560
ggcactgcta tggcctcaca caaagacgac aaagacaagt tctttcccat gagcggtgtc   1620 atgattttg gaaggagag cgccggagct tcaaacactg cattggacaa tgtcatgatc    1680
acagacgaag aggaaatcaa agccactaac cccgtggcca ccgaaagatt tgggactgtg   1740
gcagtcaatc tccagagcag cagcacagac cctgcgaccg gagatgtgca tgttatggga   1800
gccttacctg gaatggtgtg gcaagacaga gacgtatacc tgcagggtcc tatttgggcc   1860
aaaattcctc acacggatgg acactttcac ccgtctcctc tcatgggcgg ctttggactt   1920
aagcacccgc ctcctcagat cctcatcaaa aacacgcctg ttcctgcgaa tcctccggca   1980
gagttttcgg ctacaaagtt tgcttcattc atcacccagt attccacagg acaagtgagc   2040
gtggagattg aatgggagct gcagaaagaa aacagcaaac gctggaatcc cgaagtgcag   2100
tatacatcta actatgcaaa atctgccaac gttgatttca ctgtggacaa caatggactt   2160
tatactgagc ctcgccccat tggcacccgt tacctcaccc gtcccctg            2208
```

<210> SEQ ID NO 11
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 11

```
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtctggtgct tcctggctac aagtacctcg acccttcaa cggactcgac    180 aaggggagc ccgtcaacgc ggcggacgca gcggccctcg agcacgacaa ggcctacgac   240
cagcagctca aagcgggtga caatccgtac ctgcggtata accacgccga cgccgagttt   300
caggagcgtc tgcaagaaga tacgtcattt ggggcaacc tcgggcgagc agtcttccag   360
gccaagaagc gggttctcga acctctcggt ctggttgagg aaggcgctaa gacggctcct   420
gcaaagaaga ccggtagagc cgtcacct cagcgttccc ccgactcctc cacgggcatc    480
ggcaagaaag ccagcagcc cgccagaaag agactcaatt tcggtcagac tggcgactca   540
gagtcagtcc ccgaccctca acctctcgga gaacctccag cagcgccctc tagtgtggga   600
tctggtacag tggctgcagg cggtggcgca ccaatggcag acaataacga aggtgccgac   660
ggagtgggta atgcctcagg aaattggcat tgcgattcca tggctgggc gacagagtc    720 attaccacca gcacccgaac ctgggccctg cccacctaca acaaccacct ctacaagcaa   780
atctccagtg aaactgcagg tagtaccaac gacaacacct acttcggcta cagcaccccc   840
```

```
tgggggtatt ttgactttaa cagattccac tgccacttct caccacgtga ctggcagcga      900
ctcatcaaca acaactgggg attccggccc aagaagctgc ggttcaagct cttcaacatc      960
caggtcaagg aggtcacgac gaatgacggc gttacgacca tcgctaataa ccttaccagc     1020
acgattcagg tattctcgga ctcggaatac cagctgccgt acgtcctcgg ctctgcgcac     1080
cagggctgcc tgcctccgtt cccggcggac gtcttcatga ttcctcagta cggctacctg     1140
actctcaaca atggcagtca gtctgtggga cgttcctcct tctactgcct ggagtacttc     1200
ccctctcaga tgctgagaac gggcaacaac tttgagttca gctacagctt cgaggacgtg     1260
cctttccaca gcagctacgc acacagccag agcctggacc ggctgatgaa tcccctcatc     1320
gaccagtact tgtactacct ggccagaaca cagagtaacc aggaggcac agctggcaat     1380 cgggaactgc agttttacca gggcgggcct tcaactatgg ccgaacaagc caagaattgg     1440
ttacctggac cttgcttccg gcaacaaaga gtctccaaaa cgctggatca aacaacaac      1500 agcaactttg cttggactgg tgccaccaaa tatcacctga acggcagaaa ctcgttggtt     1560
aatcccggcg tcgccatggc aactcacaag gacgacgagg accgcttttt cccatccagc     1620
ggagtcctga ttttggaaa actggagca actaacaaaa ctacattgga aaatgtgtta     1680
atgacaaatg aagaagaaat tcgtcctact aatcctgtag ccacgaagaa atacgggata     1740
gtcagcagca acttacaagc ggctaatact gcagcccaga cacaagttgt caacaaccag     1800
ggagccttac ctggcatggt ctggcagaac cgggacgtgt acctgcaggg tcccatctgg     1860
gccaagattc ctcacacgga tggcaacttt caccgtctc ctttgatggg cggctttgga     1920
cttaaacatc cgcctcctca gatcctgatc aagaacactc ccgttccgc taatcctccg     1980 gaggtgttta ctcctgccaa gtttgcttcg ttcatcacac agtacagcac cggacaagtc     2040
agcgtggaaa tcgagtggga gctgcagaag gaaaacagca agcgctggaa cccggagatt     2100 cagtacaccct ccaactttga aaagcagact ggtgtggact ttgccgttga cagccagggt     2160
gtttactctg agcctcgccc tattggcact cgttacctca cccgtaatct g              2211

<210> SEQ ID NO 12
<211> LENGTH: 2214
<212> TYPE: DNA
<213> ORGANISM: Artificial Sequence
<220> FEATURE:
<223> OTHER INFORMATION: Synthetic Polynucleotide

<400> SEQUENCE: 12
atggctgccg atggttatct tccagattgg ctcgaggaca acctctctga gggcattcgc       60
gagtggtggg cgctgaaacc tggagccccg aagcccaaag ccaaccagca aaagcaggac      120
gacgccgggg tctggtgct tcctggctac aagtacctcg accccttcaa cggactcgac      180
aagggggagc ccgtcaacgc ggcggacgca gcggccctcg agcacgacaa ggcctacgac      240
cagcagctgc aggcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccggtaga gccatcaccc agcgttctc cagactcctc tacgggcatc      480
ggcaagaaag ccaacagcc cgccagaaaa agactcaatt ttggtcagac tggcgactca      540
gagtcagttc cagaccctca acctctcgga gaacctccag cagcgccctc tggtgtggga      600
cctaatacaa tggctgcagg cggtggcgca ccaatggcag acaataacga aggcgccgac      660
ggagtgggta gttcctcggg aaattggcat tgcgattcca catggctggg cgacagagtc      720
```

```
atcaccacca gcacccgaac ctgggccctg cccacctaca acaaccacct ctacaagcaa      780
atctccaacg ggacatcggg aggagccacc aacgacaaca cctacttcgg ctacagcacc      840 ccctggggt attttgactt taacagattc cactgccact tttcaccacg tgactggcag       900
cgactcatca caacaactg gggattccgg cccaagagac tcagcttcaa gctcttcaac       960
atccaggtca aggaggtcac gcagaatgaa ggcaccaaga ccatcgccaa taacctcacc     1020
agcaccatcc aggtgtttac ggactcggag taccagctgc cgtacgttct cggctctgcc     1080
caccagggct gcctgcctcc gttcccggcg gacgtgttca tgattcccca gtacggctac     1140
ctaacactca caacggtag tcaggccgtg ggacgctcct ccttctactg cctggaatac      1200
tttccttcgc agatgctgag aaccggcaac aacttccagt ttacttacac cttcgaggac    1260 gtgccttttcc acagcagcta cgcccacagc cagagcttgg accggctgat gaatcctctg    1320
attgaccagt acctgtacta cttgtctcgg actcaaacaa caggaggcac ggcaaatacg     1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga ttttggcaa acaaaatgct gccagagaca atgcggatta cagcgatgtc    1680
atgctcacca gcgaggaaga aatcaaaacc actaaccctg tggctacaga ggaatacggt    1740
atcgtggcag ataacttgca gcagcaaaac acggctcctc aaattggaac tgtcaacagc    1800 caggggggcct tacccggtat ggtctggcag aaccgggacg tgtacctgca gggtcccatc    1860
tgggccaaga ttcctcacac ggacggcaac ttccacccgt ctccgctgat gggcggcttt    1920
ggcctgaaac atcctccgcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctg          2214

<210> SEQ ID NO 13
<211> LENGTH: 2208
<212> TYPE: DNA
<213> ORGANISM: Artificial Sequence
<220> FEATURE:
<223> OTHER INFORMATION: Synthetic Polynucleotide

<400> SEQUENCE: 13
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaatacctgg acccggcaa cggactcgac      180 aagggggagc cggtcaacgc agcagacgcg gcggccctcg agcacgacaa ggcctacgac     240
cagcagctca aggccggaga caacccgtac ctcaagtaca accacgccga cgccgagttc     300
caggagcggc tcaaagaaga tacgtctttt ggggcaacc tcgggcgagc agtcttccag      360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
```

| | |
|---|---|
| tcagtcccag accctcaacc aatcggagaa cctcccgcag cccccctcagg tgtgggatct | 600 |
| cttacaatgg cttcaggtgg tggcgcacca gtggcagaca ataacgaagg tgccgatgga | 660 |
| gtgggtagtt cctcgggaaa ttggcattgc gattcccaat ggctggggga cagagtcatc | 720 |
| accaccagca cccgaacctg ggccctgccc acctacaaca atcacctcta caagcaaatc | 780 |
| tccaacagca catctggagg atcttcaaat gacaacgcct acttcggcta cagcaccccc | 840 |
| tgggggtatt ttgacttcaa cagattccac tgccacttct caccacgtga ctggcagcga | 900 |
| ctcatcaaca caactgggg attccggcct aagcgactca acttcaagct cttcaacatt | 960 |
| caggtcaaag aggttacgga caacaatgga gtcaagacca tcgccaataa ccttaccagc | 1020 |
| acggtccagg tcttcacgga ctcagactat cagctcccgt acgtgctcgg gtcggctcac | 1080 |
| gagggctgcc tcccgccgtt cccagcggac gttttcatga ttcctcagta cgggtatctg | 1140 |
| acgcttaatg atggaagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tccactcatc | 1320 |
| gaccaatact tgtactatct ctcaaagact attaacggtt ctggacagaa tcaacaaacg | 1380 |
| ctaaaattca gtgtggccgg acccagcaac atggctgtcc agggaagaaa ctacatacct | 1440 |
| ggacccagct accgacaaca acgtgtctca accactgtga ctcaaaacaa caacagcgaa | 1500 |
| tttgcttggc ctggagcttc ttctgggct ctcaatggac gtaatagctt gatgaatcct | 1560 |
| ggacctgcta tggccagcca caaagaagga gaggaccgtt tctttccttt gtctggatct | 1620 |
| ttaattttg gcaaacaagg aactggaaga gacaacgtgg atgcggacaa agtcatgata | 1680 |
| accaacgaag aagaaattaa aactactaac ccggtagcaa cggagtccta tggacaagtg | 1740 |
| gccacaaacc accagagtgc caagcacag gcgcagaccg gctgggttca aaaccaagga | 1800 |
| atacttccgg gtatggtttg caggacaga gatgtgtacc tgcaaggacc catttgggcc | 1860 |
| aaaattcctc acacggacgg caactttcac ccttctccgc tgatgggagg gtttggaatg | 1920 |
| aagcacccgc ctcctcagat cctcatcaaa acacacctg tacctgcgga tcctccaacg | 1980 |
| gccttcaaca aggacaagct gaactctttc atcacccagt attctactgg ccaagtcagc | 2040 |
| gtggagatcg agtgggagct gcagaaggaa aacagcaagc gctggaaccc ggagatccag | 2100 |
| tacacttcca actattacaa gtctaataat gttgaatttg ctgttaatac tgaaggtgta | 2160 |
| tatagtgaac cccgccccat tggcaccaga tacctgactc gtaatctg | 2208 |

<210> SEQ ID NO 14
<211> LENGTH: 2258
<212> TYPE: DNA
<213> ORGANISM: Artificial Sequence
<220> FEATURE:
<223> OTHER INFORMATION: Synthetic Polynucleotide

<400> SEQUENCE: 14

| | |
|---|---|
| tcgaggacaa cctctctgag ggcattcgcg agtggtggga cttgaaacct ggagccccga | 60 |
| aacccaaagc caaccagcaa agcaggacg acggccgggg tctggtgctt cctggctaca | 120 |
| agtacctcgg acccttcaac ggactcgaca aggggagcc cgtcaacgcg gcggacgcag | 180 |
| cggccctcga gcacgacaag gcctacgacc agcagctcaa agcgggtgac aatccgtacc | 240 |
| tgcggtataa ccacgccgac gccgagtttc aggagcgtct gcaagaagat acgtcttttg | 300 |
| ggggcaacct cgggcgagca gtcttccagg ccaagaagcg ggttctcgaa cctctcggtc | 360 |
| tggttgagga aggcgctaag acggctcctg gaaagaagag accggtagag ccatcaccc | 420 |

```
agcgttctcc agactcctct acgggcatcg gcaagaaagg ccagcagccc gcgaaaaaga    480
gactcaactt tgggcagact ggcgactcag agtcagtgcc cgaccctcaa ccaatcggag    540
aaccccccgc aggcccctct ggtctgggat ctggtacaat ggctgcaggc ggtggcgctc    600
caatggcaga caataacgaa ggcgccgacga gagtgggtag ttcctcagga aattggcatt    660
gcgattccac atggctgggc gacagagtca tcaccaccag cacccgaacc tgggccctcc    720
ccacctacaa caaccacctc tacaagcaaa tctccaacgg gacttcggga ggaagcacca    780
acgacaacac ctacttcggc tacagcaccc cctgggggta ttttgacttt aacagattcc    840
actgccactt ctcaccacgt gactggcagc gactcatcaa caacaactgg ggattccggc    900
ccaagagact caacttcaag ctcttcaaca tccaggtcaa ggaggtcacg cagaatgaag    960
gcaccaagac catcgccaat aaccttacca gcacgattca ggtctttacg gactcggaat   1020
accagctccc gtacgtcctc ggctctgcgc accagggctg cctgcctccg ttcccggcgg   1080
acgtcttcat gattcctcag tacgggtacc tgactctgaa caatggcagt caggccgtgg   1140
gccgttcctc cttctactgc ctggagtact ttccttctca aatgctgaga acgggcaaca   1200
actttgagtt cagctaccag tttgaggacg tgccttttca cagcagctac gcgcacagcc   1260
aaagcctgga ccggctgatg aaccccctca tcgaccagta cctgtactac ctgtctcgga   1320
ctcagtccac gggaggtacc gcaggaactc agcagttgct attttctcag gccgggccta   1380
ataacatgtc ggctcaggcc aaaaactggc tacccgggcc ctgctaccgg cagcaacgcg   1440
tctccacgac actgtcgcaa aataacaaca gcaactttgc ctggaccggt gccaccaagt   1500
atcatctgaa tggcagagac tctctggtaa atcccggtgt cgctatggca acccacaagg   1560
acgacgaaga gcgatttttt ccgtccagcg gagtcttaat gtttgggaaa cagggagctg   1620
gaaaagacaa cgtggactat agcagcgtta tgctaaccag tgaggaagaa attaaaacca   1680
ccaacccagt ggccacagaa cagtacgcgc tggtggccga taacctgcaa cagcaaaacg   1740
ccgctcctat tgtaggggcc gtcaacagtc aaggagcctt acctggcatg gtctggcaga   1800
accgggacgt gtacctgcag ggtcctatct gggccaagat tcctcacacg gacgaaaact   1860
ttcatccctc gccgctgatg ggaggctttg gactgaaaca cccgcctcct cagatcctga   1920
ttaagaatac acctgttccc gcggatcctc caactacctt cagtcaagct aagctggcgt   1980
cgttcatcac gcagtacagc accggacagg tcagcgtgga aattgaatgg agctgcaga    2040 aagaaaacag caaacgctgg aacccagaga ttcaatacac ttccaactac tacaaatcta   2100
caaatgtgga ctttgctgtt aacacagatg gcacttattc tgagcctcgc cccatcggca   2160
cccgttacct cacccgtaat ctgtaattgc ttgttaatca ataaaccggt tgattcgttt   2220
cagttgaact ttggtctctg cgaagggcga attcgttt                           2258
```

<210> SEQ ID NO 15
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 15

```
aggaattctg ctggaggagt gtgtcatacc tcggtagggt ccactacaca tctttctccc     60
gcagcctctc catcttcctg tgactgcggg cgcctcagcc tggctggcc agctgtgagt    120 aattctttgg cagtgtctta gctggttgtt gtgagtatta gctaaggaag caatcagcaa    180
```

| | |
|---|---|
| gtatactgcc ctagaagtgc tgcacattgt tgggccgaga aggaaaaggt cagaggtcag | 240 |
| caacgcccac acccctgaga ggcgctggac ttgcggagct gctcgaccat actggtgggt | 300 |
| atgggatggc ggccgcgtcc c | 321 |

<210> SEQ ID NO 16
<211> LENGTH: 2227
<212> TYPE: DNA
<213> ORGANISM: Artificial Sequence
<220> FEATURE:
<223> OTHER INFORMATION: Synthetic Polynucleotide

<400> SEQUENCE: 16

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt cggtacaatt cacgcgtcga cattgattat tgactctggt cgttacataa | 180 |
| cttacggtaa atggcccgcc tggctgaccg cccaacgacc cgcccattg acgtcaataa | 240 |
| tgacgtatgt tcccatagta acgccaatag ggactttcca ttgacgtcaa tgggtggagt | 300 |
| atttacggta aactgcccac ttggcagtac atcaagtgta tcatatgcca agtacgcccc | 360 |
| ctattgacgt caatgacggt aaatggcccg cctggcatta tgcccagtac atgacccttat | 420 |
| gggactttcc tacttggcag tacatctact cgaggccacg ttctgcttca ctctccccat | 480 |
| ctccccccc tccccacccc caattttgta tttatttatt ttttaattat tttgtgcagc | 540 |
| gatggggcg gggggggggg ggggggggc gcgcgccagg cggggcgggg cggggcgagg | 600 |
| ggcggggcgg ggcgaggcgg agaggtgcgg cggcagccaa tcagagcggc gcgctccgaa | 660 |
| agtttccttt tatggcgagg cggcggcggc ggcggcccta taaaaagcga agcgcgcggc | 720 |
| gggcgggagc gggatcagcc accgcggtgg cggcctaga gtcgatcgag gaactgaaaa | 780 |
| accagaaagt taactggtaa gtttagtctt tttgtctttt atttcaggaa ttctgctgga | 840 |
| ggagtgtgtc atacctcggt agggtccact acacatcttt ctcccgcagc ctctccatct | 900 |
| tcctgtgact gcgggcgcct cagcctgggc tggccagctg tgagtaattc tttggcagtg | 960 |
| tcttagctgg ttgttgtgag tattagctaa ggaagcaatc agcaagtata ctgccctaga | 1020 |
| agtgctgcac attgttgggc cgagaaggaa aaggtcagag gtcagcaacg cccacacccc | 1080 |
| tgagaggcgc tggacttgcg gagctgctcg accatactgg tgggtatggg atggcggccg | 1140 |
| cgtcccggat ccggtggtgg tgcaaatcaa agaactgctc ctcagtggat gttgccttta | 1200 |
| cttctaggcc tgtacggaag tgttacttct gctctaaaag ctgcggaatt gtacccgcgg | 1260 |
| ccgatccacc ggtcgccacc atctagcatg ggagtcaaag ttctgtttgc cctgatctgc | 1320 |
| atcgctgtgg ccgaggccaa gcccaccgag aacaacgaag acttcaacat cgtggccgtg | 1380 |
| gccagcaact tcgcgaccac ggatctcgat gctgaccgcg gaagttgcc cggcaagaag | 1440 |
| ctgccgctgg aggtgctcaa agagatgaa gccaatgccc ggaaagctgg ctgcaccagg | 1500 |
| ggctgtctga tctgcctgtc ccacatcaag tgcacgccca agatgaagaa gttcatccca | 1560 |
| ggacgctgcc acacctacga aggcgacaaa gagtccgcac agggcggcat aggcgaggcg | 1620 |
| atcgtcgaca ttcctgagat tcctgggttc aaggacttgg agcccatgga gcagttcatc | 1680 |
| gcacaggtcg atctgtgtgt ggactgcaca actggctgcc tcaaagggct tgccaacgtg | 1740 |
| cagtgttctg acctgctcaa gaagtggctg ccgcaacgct gtgcgacctt gccagcaag | 1800 |
| atccagggcc aggtggacaa gatcaagggg gccggtggtg actagctcga cgctgatcag | 1860 |
| cctcgactgt gccttctagt tgccagccat ctgttgtttg ccctccccc gtgccttcct | 1920 |

```
tgaccctgga aggtgccact cccactgtcc tttcctaata aaatgaggaa attgcatcgc    1980
attgtctgag taggtgtcat tctattctgg ggggtggggt ggggcaggac agcaaggggg    2040
aggattggga agacaattag gtagataagt agcatggcgg gttaatcatt aactacaagg    2100 aaccoctagt gatggagttg gccactccct ctctgcgcgc tcgctcgctc actgaggccg    2160
ggcgaccaaa ggtcgcccga cgcccgggct ttgcccgggc ggcctcagtg agcgagcgag    2220
cgcgcag                                                              2227
```

PROSTATE-TARGETING ADENO-ASSOCIATED VIRUS SEROTYPE VECTORS

RELATED APPLICATIONS

This application is a National Stage Application of PCT/US2016/058185, filed Oct. 21, 2016, entitled "PROSTATE-TARGETING ADENO-ASSOCIATED VIRUS SEROTYPE VECTORS", which claims the benefit under 35 U.S.C. § 119(e) of U.S. Provisional Application Ser. No. 62/245,027, filed Oct. 22, 2015, and U.S. Provisional Application Ser. No. 62/322,285, filed Apr. 14, 2016, the entire contents of each application which are incorporated herein by reference.

BACKGROUND

The prostate is an exocrine gland that is crucial to constituting the male reproductive system, and the functions of prostate are similar in the majority of mammals despite anatomical differences. Three types of prostate diseases are the major threats for the health of prostate, i.e., prostatitis, benign prostate hyperplasia (BPH) and prostate cancer. Together, these prostate diseases are severely compromising the life quality and life span of males, especially for the aged male population. For example, BPH is one of the top ten most costly diseases among male populations over 50-year old in the USA, and prostate cancer is the second most diagnosed malignancy and the sixth leading cause for mortality of all cancers in males worldwide.

To date, many efforts have been made to prevent or to treat prostate diseases, including surgery, medication, and radiotherapy. Nevertheless, highly effective clinical interventions for a variety of prostate diseases are still lacking. For example, although the early stage of prostate cancer can be prevented with hormonal therapy, most hormone-dependent prostate cancers will eventually develop into castration-resistant prostate cancer (CRPC). So far, no effective treatment exists for CRPC. As the genetic basis of prostate diseases was gradually unraveled during the past decades, gene therapy was explored as a therapeutic strategy for prostate diseases, and researchers have demonstrated the feasibility of several gene therapy approaches to treating BPH and prostate cancer in mice using various types of viral gene delivery vectors. However, many viral vectors, such as adenovirus, lentivirus and retrovirus, can cause insertional genotoxicity and/or immunotoxicity, which greatly limits their clinical use.

SUMMARY

Adeno-associated virus (AAV) is a single-stranded DNA virus, and recombinant AAV (rAAV) vectors possess many advantages in gene therapy applications, including low immunogenicity and genotoxicity, broad tissue tropism and high transduction efficiency in vivo, and long-term transgene expression. Aspects of the invention are related to the discovery that rAAV vectors comprising capsid proteins having a certain serotype, including, but not limited to, AAV5, AAV6.2, AAV7, AAV8, AAV9, AAVrh.10, mediate delivery of transgenes to prostate tissue more efficiently than other vectors (e.g., rAAV vectors comprising other capsid protein serotypes).

Accordingly in some aspects, the disclosure provides a method for delivering a transgene to prostate tissue, the method comprising: administering to prostate tissue of a subject an effective amount of rAAV, wherein the rAAV comprises (i) a capsid protein having a serotype selected from the group consisting of AAV5, AAV6, AAV6.2, AAV7, AAV8, AAV9, and AAVrh.10, and (ii) a nucleic acid comprising a promoter operably linked to a transgene.

In some aspects, the disclosure provides a method for treating a prostate disease, the method comprising: administering to a subject having or suspected of having a prostate disease an effective amount of rAAV, wherein the rAAV comprises (i) a capsid protein having a serotype selected from the group consisting of AAV5, AAV6.2, AAV7, AAV8, AAV9, and AAVrh.10, and (ii) a nucleic acid comprising a promoter operably linked to a transgene.

In some embodiments, the capsid protein comprises an amino acid sequence that is at least 70%, at least 80%, at least 90%, at least 95%, or at least 99% identical to any one of SEQ ID NO: 1-7. In some embodiments, the capsid protein comprises an amino acid sequence as set forth in SEQ ID NO: 3 or 4. In some embodiments, the capsid protein is AAV6.2 capsid protein (SEQ ID NO: 3) or AAV7 capsid protein (SEQ ID NO: 4).

In some embodiments, the transgene encodes a gene associated with a prostate disease. In some embodiments, the prostate disease is selected from prostatitis, prostate cancer and benign prostate hyperplasia (BPH). In some embodiments, the gene encodes a tumor suppressor molecule (e.g., a tumor suppressor protein or a miRNA that regulates tumor suppression). In some embodiments, the gene encodes BCL-2, PTEN, SLC39A1, BRCA1, BRCA2, HPC1, RUNX2, CLCA2, YAP1, MASPIN, LL37, CDKN1B, AR, NKX3.1, CASP9, FKHR, GSK3, MDM2, ERK1/2, PSA, CCND1, ALDOA, Sox4, CD44, and miR34a.

In some aspects, the disclosure is based on the discovery that miR34a expression is downregulated in prostate cancer cells. In some embodiments, overexpression of miR34a in prostate cancer cells results in decreased cancer cell viability and migration. Accordingly, in some aspects, the disclosure provides a method for treating a prostate disease, the method comprising: administering to a subject having or suspected of having a prostate disease an effective amount of a nucleic acid comprising a promoter operably linked to a transgene, wherein the transgene encodes miR34a. In some embodiments, the transgene comprises or consists of a nucleic acid having a sequence as set forth in SEQ ID NO: 15. In some embodiments, the nucleic acid comprises or consists of a nucleic acid having a sequence as set forth in SEQ ID NO: 16.

In some embodiments, the administration occurs by injection. In some embodiments, the injection is not intraperitoneal injection (i.p.). In some embodiments, the injection is intraprostate injection.

In some embodiments, the administration results in transduction of a prostate cell type selected from the group consisting of luminal prostate cells, basal prostate cells, and stromal prostate cells. In some embodiments, the administration results in transduction of at least two of the following prostate cell types: luminal prostate cells, basal prostate cells, and stromal prostate cells.

In some embodiments, the rAAV further comprises two AAV inverted terminal repeats (ITRs), wherein the ITRs flank the transgene. In some embodiments, the AAV ITRs are ITRs of one or more serotypes selected from: AAV2, AAV3, AAV4, AAV5, and AAV6.

In some embodiments, the subject is a mammal, optionally a human.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

FIG. 2A shows representative fluorescence images of anterior prostate (AP) cryo-sections showing the merge of EGFP native fluorescence and nuclear staining by DAPI following injections of each of 12 rAAV serotypes or PBS. Squared regions indicate the locations of high magnification images shown in (FIG. 2B). Scale bars represent 100 microns. FIG. 2B shows high magnification images of AP cryo-sections following PBS injection or transduction with rAAV6.2 and 7. Scale bars represent 25 microns.

FIG. 3A shows representative fluorescence images of dorsal lateral prostate (DLP) cryo-sections showing the merge of EGFP native fluorescence and nuclear staining by DAPI following injections of each of 12 rAAV serotypes or PBS. Squared regions indicate the locations of high magnification images shown in (FIG. 3B). Scale bars represent 100 microns. FIG. 3B shows high magnification images of DLP cryo-sections following PBS injection or transduction with rAAV6.2 and 7. Scale bars represent 25 microns.

FIGS. 4A-4B show rAAV6.2 and rAAV7 efficiently transduced mouse prostate following intraprostate injection. FIG. 4A shows quantification of transduction efficiency in AP (gray bars) and DLP (black bars) following intraprostate injection with rAAV vectors of different serotypes expressing EGFP. EGFP fluorescence intensity of cryo-sections is presented in arbitrary units (a.u.). FIG. 4B shows biodistribution of rAAV genomes in AP (gray bars) and DLP (black bars) following intraprostate injection of rAAV6.2 and rAAV7. Data are presented as rAAV genome copies per diploid genome.

FIGS. 6A-6B show rAAV6.2 and 7 could transduce the majority of major prostatic cell types following intraprostate injection. FIG. 6A shows representative images of immunofluorescence staining of prostate luminal cells (top panels), basal cells (middle panels) and stromal cells (bottom panels), marked by K8, K5 and α-actin staining, respectively. Nuclear staining by DAPI, native EGFP fluorescence images and merged images from the same sections are also shown. Arrows indicate representative co-localization of EGFP signal and cell type marker signal. FIG. 6B shows quantification of the percentage of EGFP-positive cells of each cell type.

FIG. 7A shows qPCR data indicating that miR34a is significantly downregulated in the prostate of TRAMP mice compared to wild type (WT) mice. FIG. 7B shows a luciferase assay demonstrating rAAV-miR34 (pAAVsc-CB PI-miR34a-Gluc) successfully downregulates reporter gene (LacZ/Fluc) expression in vitro.

FIG. 8A shows qPCR data demonstrating relative expression level of miR34a in control (mock) and miR34a-treated cells 48 hours post-transfection. FIG. 8B shows a schematic diagram of a prostate cancer cell cycle, highlighting the $G_1$ (2N) and S (2N-4N) phases. FIG. 8C shows transfection with miR34a results in a significant increase in 2N cells compared to mock transfected cells. FIG. 8D shows transfection with miR34a results in a significant decrease in 2N-4N cells compared to mock transfected cells. FIG. 8E shows miR34a overexpression decreases target gene expression (CCND1, TOP2A, and CD44) in vitro.

FIG. 9A shows overexpression of miR34a results in a decrease in cell viability of miR34a treated PC3 cells compared to control (Mock) PC3 cells. FIG. 9B shows a significant decrease in OD450 of miR34a-treated PC3 cells compared to control (Mock) PC3 cells. FIG. 9C shows overexpression of miR34a results in reduced PC3 cell migration compared to untreated cells, as measured by a wound healing assay. FIG. 9D shows overexpression of miR34a results in a significant increase in wound width, indicating a reduction in cell migration, compared to control (Mock) cells.

FIG. 10A shows 2-month old TRAMP mice intraprostatically injected with rAAV7-miR34a ($4\times10^{11}$ GC/mouse) have a significantly lower body weight (e.g., less tumor growth) than PBS-treated control mice. FIG. 10B shows 2-month old TRAMP mice intraprostatically injected with rAAV7-miR34a ($4\times10^{11}$ GC/mouse) have a significantly improved survival rates (measured by percent survival) compared to PBS-treated control mice.

FIG. 12A shows relative expression of miR34a is significantly increased in miR34a-treated mouse prostate compared to PBS-injected control mice. FIG. 12B shows reporter gene (Gluc) expression persists up to 52 weeks post-intraprostatic injection of rAAV-miR34a-Gluc. FIG. 12C shows mice treated with miR34a show significant decreases in ALDOA and Sox4 expression compared to PBS-injected control mice 3 weeks post-injection.

DETAILED DESCRIPTION

Figure 1:
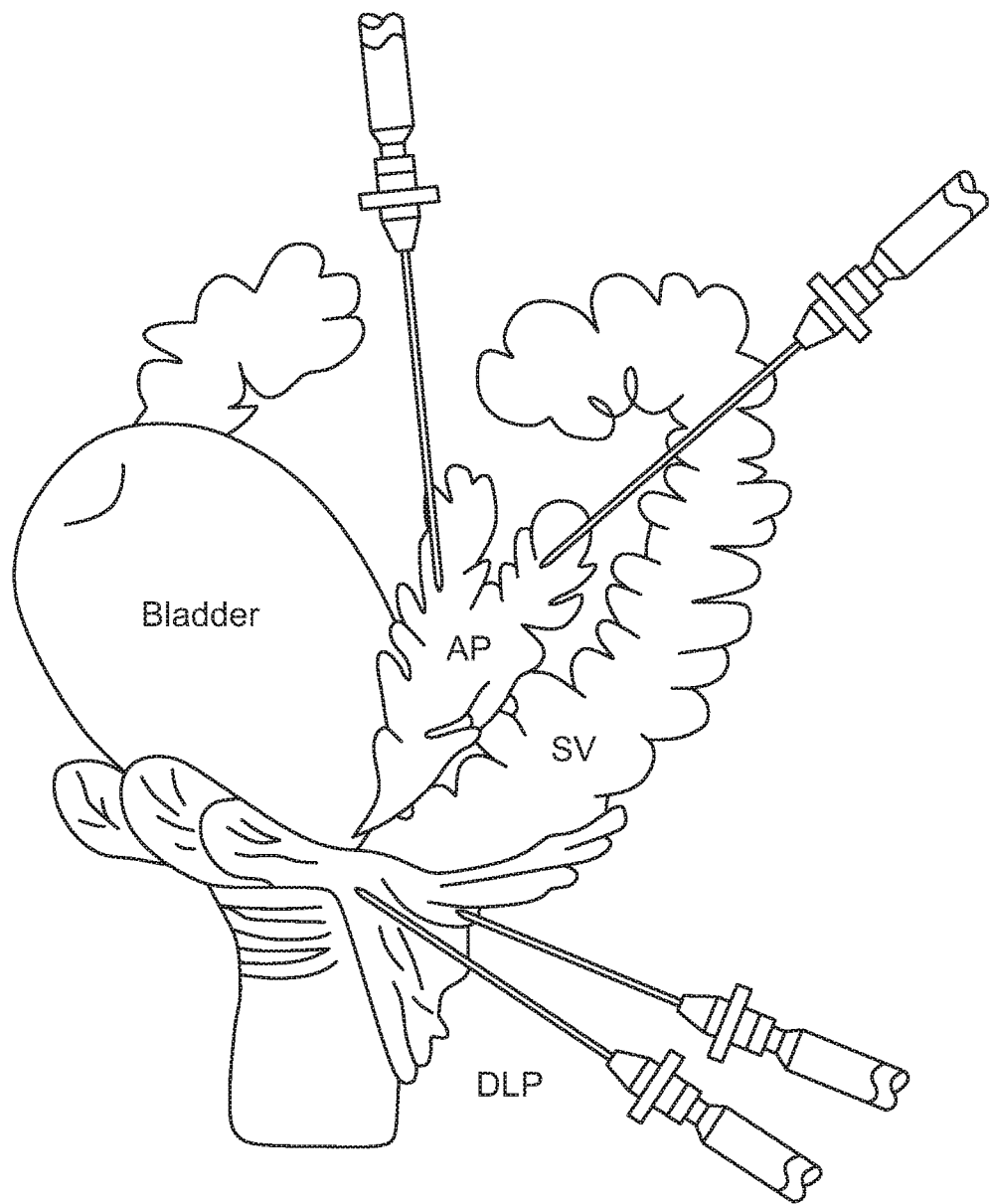
FIG. 1 shows a graphical depiction of the anatomical structure of mouse prostate and intraprostate injection sites. $1\times10^{11}$ GC per injection site of rAAV vectors were delivered into four sites as indicated by the syringes, namely the two lobes of the anterior prostate (AP) and two sites in the dorsal lateral prostate (DLP). SV: seminal vesicle.

The disclosure relates in some aspects to compositions and methods for tissue-specific delivery of a transgene by a recombinant adeno-associated virus (rAAV). The invention relates, in part, to the discovery that rAAV vectors comprising a capsid protein(s) having a certain serotype (e.g., AAV5, AAV6.2, AAV7, AAV8, AAV9, and AAVrh.10) mediate delivery of transgenes to prostate tissue more efficiently than rAAV vectors comprising other capsid protein serotypes.
Methods and Compositions for AAV-Mediated Delivery of a Transgene to Prostate Tissue Methods for delivering a transgene to prostate tissue in a subject are provided herein. The methods typically involve administering to a subject an effective amount of a rAAV comprising a nucleic acid for expressing a transgene in the subject. An "effective amount" of a rAAV is an amount sufficient to infect a sufficient number of cells of a target tissue in a subject. In some embodiments, a target tissue is prostate tissue. An effective amount of a rAAV may be an amount sufficient to have a therapeutic benefit in a subject, e.g., to extend the lifespan of a subject, to improve in the subject one or more symptoms of disease, e.g., a symptom of prostate disease (e.g., prostatitis, BPH, prostate cancer, etc.). In some cases, an effective amount of a rAAV may be an amount sufficient to produce a stable somatic transgenic animal model. The effective amount will depend on a variety of factors such as, for example, the species, age, weight, health of the subject, and the prostate tissue to be targeted, and may thus vary among subject and tissue.

An effective amount may also depend on the rAAV used. The invention is based, in part on the recognition that rAAV comprising capsid proteins having a particular serotype (e.g., AAV5, AAV6.2, AAV7, AAV8, AAV9, and AAVrh.10) mediate more efficient transduction of prostate tissue that rAAV comprising capsid proteins having a different serotype. Thus in some embodiments, the rAAV comprises a capsid protein of an AAV serotype selected from the group consisting of: AAV5, AAV6.2, AAV7, AAV8, AAV9, and AAVrh.10 (SEQ ID NO: 1 to 6). In some embodiments, the rAAV comprises a capsid protein of AAV6.2 serotype (SEQ ID NO: 3) or AAV7 serotype (SEQ ID NO: 4). In some embodiments, the capsid protein comprises an amino acid sequence that is at least 70%, at least 80%, at least 90%, at least 95%, or at least 99% identical to any one of SEQ ID NO: 1-7. In some embodiments, the capsid protein is AAV6.2 capsid protein (SEQ ID NO: 3) or AAV7 capsid protein (SEQ ID NO: 4).

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the mode of administration. For example, targeting a prostate tissue by intravenous administration or intraperitoneal injection may require different (e.g., higher) doses, in some cases, than targeting prostate tissue by intraprostate injection. The invention is based, in part, on the recognition that intraperitoneal injection (i.p.) of rAAV does note mediate efficient transduction of prostate cells. Thus, in some embodiments, the injection is not intraperitoneal injection (i.p.). In some embodiments, the injection is intraprostate injection. Intraprostate injection can be transperineal, transrectal, or transurethral, as described, for example, in Saemi et al., Indian J Urol. July-September; 24(3): 329-335; 2008. In some cases, multiple doses of a rAAV are administered.

Generally, the anatomy of the prostate can be classified in two ways: lobes and zones. For example, in humans the prostate gland has four distinct glandular regions under the zone classification: the peripheral zone (PZ), central zone (CZ), transition zone (TZ), and stroma. Under the lobe classification, the human prostate comprises four lobes: anterior lobe, posterior lobe, lateral lobe, and median lobe. In other species different terminology may be used to refer to different prostate structures, for example, in mouse prostate sites are referred to using anatomical positions, e.g., an anterior prostate, a dorsal lateral prostate, etc. See, for example, Selth, et al. International Journal of Cancer. 131 (3):652-661, 2012, and Wang, et al. Cancer Cell. 4(3):209-221, 2003. No matter the classification system, prostate tissue comprises at least three cell types: luminal prostate cells, basal prostate cells, and stromal prostate cells. In some embodiments, administration of an rAAV as described herein results in transduction of a prostate cell type selected from the group consisting of luminal prostate cells, basal prostate cells, and stromal prostate cells. In some embodiments, the administration results in transduction of at least two of the following prostate cell types: luminal prostate cells, basal prostate cells, and stromal prostate cells.

Prostate tissue can be healthy prostate tissue (e.g., prostate tissue not having a disease, or at risk of developing a prostate disease) or diseased prostate tissue (e.g., prostate tissue having prostatitis, BPH, or prostate cancer). As used herein, "at risk of developing a prostate disease" refers to a subject having an increased probability of developing a prostate disease than the general population due to the presence of a risk factor. Examples categories of risk factors for developing prostate disease include, but are not limited to: exposure to carcinogens (e.g., Agent Orange), kallikrein levels (e.g., PSA levels) age, race, family history (e.g., positive family history of prostate cancer), vasectomy, and dietary fat intake, for example as described in Pienta et al. Ann Intern Med. 118(10):793-803, 1993 and Carter et al. JAMA. 267(16):2215-2220, 1992.

Without wishing to be bound by any particular theory, efficient transduction of luminal, basal, and/or stromal prostate cells by rAAV described herein may be useful for the treatment of a subject having a prostate disease. Accordingly, methods and compositions for treating prostate disease are also provided herein. In some aspects, the disclosure provides a method for treating a prostate disease, the method comprising: administering to a subject having or suspected of having a prostate disease an effective amount of rAAV, wherein the rAAV comprises (i) a capsid protein having a serotype selected from the group consisting of AAV5, AAV6.2, AAV7, AAV8, AAV9, and AAVrh.10, and (ii) a nucleic acid comprising a promoter operably linked to a transgene.

As used herein, a "prostate disease" is a disease or condition of the prostate. Non-limiting examples of prostate diseases include, but are not limited to, prostatitis (e.g., acute prostatitis, chronic prostatitis), benign prostate hyperplasia (BPH), prostate cancer (e.g., acinar adenocarcinoma, ductal adenocarcinoma, transitional cell (urothelial cancer), squamous cell prostate cancer, carcinoid tumor of the prostate, small cell prostate cancer, prostate sarcoma (leiomyosarcoma), etc.).

Without wishing to be bound by any particular theory, rAAV-based delivery of a transgene encoding a gene associated with a prostate disease is useful for treatment of subjects having prostate disease. As used herein, "gene associated with a prostate disease" refers to any gene, wherein expression of that gene that provides a therapeutic benefit in a subject, e.g., to improve in the subject one or more symptoms of disease, e.g., a symptom of prostate disease (e.g., prostatitis, BPH, prostate cancer, etc.). A gene associated with prostate disease can be a protein, polypeptide, antibody or fragment thereof (e.g., ScFv), toxin, or interfering RNA. Examples of genes associated with prostate disease include, but are not limited to Bcl-2, protein kinase C, clusterin, miR34a, miR375, NKX3.1, PTEN, Maspin, CLCA2, and PMSA. Other examples of genes associated with prostate disease are known in the art and are described, for example, in Cooper et al., Nat Clin Pract Urol. December; 4(12):677-87; 2007. In some embodiments, a gene associated with prostate disease is a microRNA, for example miR34a. In some embodiments, miR34a comprises a nucleic acid sequence as set forth in SEQ ID NO: 15.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure provides an rAAV having a capsid appropriate for targeting prostate tissue. In some embodiments, the capsid has a serotype selected from the group consisting of AAV5, AAV6.2, AAV7, AAV8, AAV9, and AAVrh.10. In some embodiments, the capsid has an AAV6.2 serotype (e.g., SEQ ID NO: 3) or an AAV7 serotype (e.g., SEQ ID NO: 4). The skilled artisan also recognizes that rAAV described herein may comprise variants of AAV5, AAV6.2, AAV7, AAV8, AAV9, and AAVrh.10 serotype capsid proteins. In some embodiments, the capsid protein comprises an amino acid sequence that is at least 70%, at least 80%, at least 90%, at least 95%, or at least 99% identical to any one of SEQ ID NO: 1-7.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene associated with a prostate disease. In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., gRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene is a gene associated with a prostate disease. In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV3, AAV4, AAV5, and AAV6.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken (3-actin promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan. In some embodiments, the promoter is a prostate-specific promoter, for example a prostate-specific antigen (PSA) promoter, a probasin promoter, a Moloney murine leukemia virus long terminal repeat (MMTV LTR) promoter, etc.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

miRNAs

In some aspects, the disclosure relates to delivery of a transgene encoding microRNA 34a (miR34a) to a cell. miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

Without wishing to be bound by any particular theory, miR34a is known to function as a regulator of tumor suppression in cells. Accordingly, in some embodiments, delivery of a transgene encoding miR34 to a cell is useful for treatment of certain diseases characterized by reduction of miR34a expression or activity (e.g., certain cancers). Examples of cancers characterized by a reduction of miR34a expression or activity include but are not limited to prostate cancer, pancreatic cancer, breast cancer, colorectal cancer, cervical cancer, certain brain cancers (e.g., glioblastoma, medulloblastoma, etc.). In some embodiments, miR34a regulates cancer stem cells, such as prostate cancer stem cells, lung cancer stem cells, etc., for example as described in Misso et al. (2014) *Mol. Ther. Nucleic Acids* 3, e194; doi:10.1038/mtna.2014.47.

Thus, in some embodiments, the disclosure provides a method for treating cancer, the method comprising delivering a transgene encoding miR34a to a subject having a cancer characterized by a reduction in mir34a expression or activity.

In some aspects, the disclosure relates to the discovery that overexpression of certain miRNAs (e.g., miR34a) reduces prostate cancer cell viability and cell migration. Accordingly, in some aspects, the disclosure provides methods and compositions for treating prostate cancer by overexpressing miRNAs (e.g., miR34a) in a subject in need thereof. miRNAs and other small interfering nucleic acids regulate gene expression via target RNA transcript cleavage/degradation or translational repression of the target messenger RNA (mRNA).

In some embodiments, a miR34a miRNA described by the disclosure comprises or consists of a nucleic acid sequence as set forth in SEQ ID NO: 15. Variants of SEQ ID NO: 15 are also contemplated by the disclosure. For example, in some embodiments, a miR34a sequence is at least 75%, at least 80%, at least 85%, at least 90%, at least 95%, or at least 99% identical to SEQ ID NO: 15.

It should be appreciated that, in some embodiments, a miR34a miRNA is an inhibitory nucleic acid (e.g., miRNA, pri-miRNA, amiRNA, dsRNA, shRNA, siRNA, etc.) that is complementary with and specifically binds to a target site sequence (e.g., a miR34a binding site) of a gene (e.g., CCND1, TOP2A, CD44, etc.) and inhibits expression of the target sequence (e.g., inhibits transcription, translation, or production a protein encoded by the target sequence). In some embodiments, a target sequence comprises at least 5 contiguous nucleotides that are complementary with a sequence as set forth in SEQ ID NO: 15.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject may be by, for example, intraprostate injection. In some embodiments, the intraprostate injection is transperineal, transrectal, or transurethral injection. In some embodiments, the injection is not intraperitoneal injection (i.p.).

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., prostate tissue) and to provide sufficient levels of gene transfer and expression without undue adverse effects. Examples of pharmaceutically acceptable routes of administration include, but are not limited to, direct delivery to the selected organ (e.g., intraprostate delivery to the prostate), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^{11}$ or $10^{12}$ rAAV genome copies is effective to target prostate tissue. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to prostate tissue. However, in certain circumstances it may be desirable to separately or in addition deliver the rAAV-based therapeutic constructs via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by intraprostate injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S.

Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing a rAAV, the kit comprising a container housing an isolated nucleic acid encoding an AAV capsid protein selected from any one of SEQ ID NO: 1-7. In some embodiments, the kit further comprises instructions for producing the rAAV. In some embodiments, the kit further comprises at least one container housing a recombinant AAV vector, wherein the recombinant AAV vector comprises a transgene (e.g., a gene associated with prostate disease).

In some embodiments, the instant disclosure relates to a kit comprising a container housing a recombinant AAV having an isolated AAV capsid protein having an amino acid sequence as set forth in SEQ ID NO: 3 or SEQ ID NO: 4.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

---

Sequences

```
>AAV5 capsid protein amino acid sequence (SEQ ID NO: 1)
MSFVDHPPDWLEEVGEGLREFLGLEAGPPKPKPKPNQQHQDQARGLVLPGYNYLGPGN
GLDRGEPVNRADEVAREHDISYNEQLEAGDNPYLKYNHADAEFQEKLADDTSFGGN
LGKAVFQAKKRVLEPFGLVEEGAKTAPTGKRIDDHFPKRKKARTEEDSKPSTSSDAE
```

```
                            Sequences

AGPSGSQQLQIPAQPASSLGADTMSAGGGGPLGDNNQGADGVGNASGDWHCDSTW
MGDRVVTKSTRTWVLPSYNNHQYREIKSGSVDGSNANAYFGYSTPWGYFDFNRFHS
HWSPRDWQRLINNYWGFRPRSLRVKIFNIQVKEVTVQDSTTTIANNLTSTVQVFTDD
DYQLPYVVGNGTEGCLPAFPPQVFTLPQYGYATLNRDTNENPTERSSFFCLEYFPSK
MLRTGNNFEFTYNFEEVPFHSSFAPSQNLFKLANPLVDQYLYRFVSTNNTGGVQFNK
NLAGRYANTYKNWFPGPMGRTQGWNLGSGVNRASVSAFATTNRMELEGASYQVPP
QPNGMTNNLQGSNTYALENTMIFNSQPANPGTTATYLEGNMLITSESETQPVNRVAY
NVGGQMATNNQSSTTAPATGTYNLQEIVPGSVWMERDVYLQGPIWAKIPETGAHFH
PSPAMGGFGLKHPPPMMLIKNTPVPGNITSFSDVPVSSFITQYSTGQVTVEMEWELKK
ENSKRWNPEIQYTNNYNDPQFVDFAPDSTGEYRTTRPIGTRYLTRPL

>AAV6 capsid protein amino acid sequence (SEQ ID NO: 2)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPFGLVEEGAKTAPGKKRPVEQSPQEPDSSSGIGKTGQQP
AKKRLNFGQTGDSESVPDPQPLGEPPATPAAVGPTTMASGGGAPMADNNEGADGV
GNASGNWHCDSTWLGDRVITTSTRTWALPTYNNHLYKQISSASTGASNDNHYFGYS
TPWGYFDFNRFHCHFSPRDWQRLINNNWGFRPKRLNFKLFNIQVKEVTTNDGVTTIA
NNLTSTVQVFSDSEYQLPYVLGSAHQGCLPPFPADVFMIPQYGYLTLNNGSQAVGRS
SFYCLEYFPSQMLRTGNNFTFSYTFEDVPFHSSYAHSQSLDRLMNPLIDQYLYYLNRT
QNQSGSAQNKDLLFSRGSPAGMSVQPKNWLPGPCYRQQRVSKTKTDNNNSNFTWT
GASKYNLNGRESIINPGTAMASHKDDKDKFFPMSGVMIFGKESAGASNTALDNVMIT
DEEEIKATNPVATERFGTVAVNLQSSSTDPATGDVHVMGALPGMVWQDRDVYLQG
PIWAKIPHTDGHFHPSPLMGGFGLKHPPPQILIKNTPVPANPPAEFSATKFASFITQYST
GQVSVEIEWELQKENSKRWNPEVQYTSNYAKSANVDFTVDNNGLYTEPRPIGTRYL
TRPL >AAV6.2 capsid protein amino acid sequence (SEQ ID NO: 3)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPGKKRPVEQSPQEPDSSSGIGKTGQQP
AKKRLNFGQTGDSESVPDPQPLGEPPATPAAVGPTTMASGGGAPMADNNEGADGV
GNASGNWHCDSTWLGDRVITTSTRTWALPTYNNHLYKQISSASTGASNDNHYFGYS
TPWGYFDFNRFHCHFSPRDWQRLINNNWGFRPKRLNFKLFNIQVKEVTTNDGVTTIA
NNLTSTVQVFSDSEYQLPYVLGSAHQGCLPPFPADVFMIPQYGYLTLNNGSQAVGRS
SFYCLEYFPSQMLRTGNNFTFSYTFEDVPFHSSYAHSQSLDRLMNPLIDQYLYYLNRT
QNQSGSAQNKDLLFSRGSPAGMSVQPKNWLPGPCYRQQRVSKTKTDNNNSNFTWT
GASKYNLNGRESIINPGTAMASHKDDKDKFFPMSGVMIFGKESAGASNTALDNVMIT
DEEEIKATNPVATERFGTVAVNLQSSSTDPATGDVHVMGALPGMVWQDRDVYLQG
PIWAKIPHTDGHFHPSPLMGGFGLKHPPPQILIKNTPVPANPPAEFSATKFASFITQYST
GQVSVEIEWELQKENSKRWNPEVQYTSNYAKSANVDFTVDNNGLYTEPRPIGTRYL
TRPL >AAV7 capsid protein amino acid sequence (SEQ ID NO: 4)
MAADGYLPDWLEDNLSEGIREWWDLKPGAPKPKANQQKQDNGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPAKKRPVEPSPQRSPDSSTGIGKKGQQ
PARKRLNFGQTGDSESVPDPQPLGEPPAAPSSVGSGTVAAGGGAPMADNNEGADGV
GNASGNWHCDSTWLGDRVITTSTRTWALPTYNNHLYKQISSETAGSTNDNTYFGYS
TPWGYFDFNRFHCHFSPRDWQRLINNNWGFRPKKLRFKLFNIQVKEVTTNDGVTTIA
NNLTSTIQVFSDSEYQLPYVLGSAHQGCLPPFPADVFMIPQYGYLTLNNGSQSVGRSS
FYCLEYFPSQMLRTGNNFEFSYSFEDVPFHSSYAHSQSLDRLMNPLIDQYLYYLARTQ
SNPGGTAGNRELQFYQGGPSTMAEQAKNWLPGPCFRQQRVSKTLDQNNNSNFAWT
GATKYHLNGRNSLVNPGVAMATHKDDEDRFFPSSGVLIFGKTGATNKTTLENVLMT
NEEEIRPTNPVATEEYGIVSSNLQAANTAAQTQVVNNQGALPGMVWQNRDVYLQGP
IWAKIPHTDGNFHPSPLMGGFGLKHPPPQILIKNTPVPANPPEVFTPAKFASFITQYSTG
QVSVEIEWELQKENSKRWNPEIQYTSNFEKQTGVDFAVDSQGVYSEPRPIGTRYLTR
NL >AAV8 capsid protein amino acid sequence (SEQ ID NO: 5)
MAADGYLPDWLEDNLSEGIREWWALKPGAPKPKANQQKQDDGRGLVLPGYKYLG
PFNGLDKGEPVNAADAAALEHDKAYDQQLQAGDNPYLRYNHADAEFQERLQEDTS
FGGNLGRAVFQAKKRVLEPLGLVEEGAKTAPGKKRPVEPSPQRSPDSSTGIGKKGQQ
PARKRLNFGQTGDSESVPDPQPLGEPPAAPSGVGPNTMAAGGGAPMADNNEGADG
VGSSSGNWHCDSTWLGDRVITTSTRTWALPTYNNHLYKQISNGTSGGATNDNTYFG
YSTPWGYFDFNRFHCHFSPRDWQRLINNNWGFRPKRLSFKLFNIQVKEVTQNEGTKT
IANNLTSTIQVFTDSEYQLPYVLGSAHQGCLPPFPADVFMIPQYGYLTLNNGSQAVGR
SSFYCLEYFPSQMLRTGNNFQFTYTFEDVPFHSSYAHSQSLDRLMNPLIDQYLYYLSR
TQTTGGTANTQTLGFSQGGPNTMANQAKNWLPGPCYRQQRVSTTTGQNNNSNFAW
TAGTKYHLNGRNSLANPGIAMATHKDDEERFFPSNGILIFGKQNAARDNADYSDVM
LTSEEEIKTTNPVATEEYGIVADNLQQQNTAPQIGTVNSQGALPGMVWQNRDVYLQ
GPIWAKIPHTDGNFHPSPLMGGFGLKHPPPQILIKNTPVPADPPTTFNQSKLNSFITQYS
TGQVSVEIEWELQKENSKRWNPEIQYTSNYYKSTSVDFAVNTEGVYSEPRPIGTRYL
TRNL
```

Sequences

>AAV9 capsid protein amino acid sequence (SEQ ID NO: 6)
MAADGYLPDWLEDNLSEGIREWWALKPGAPQPKANQQHQDNARGLVLPGYKYLG
PGNGLDKGEPVNAADAAALEHDKAYDQQLKAGDNPYLKYNHADAEFQERLKEDTS
FGGNLGRAVFQAKKRLLEPLGLVEEAAKTAPGKKRPVEQSPQEPDSSAGIGKSGAQP
AKKRLNFGQTGDTESVPDPQPIGEPPAAPSGVGSLTMASGGGAPVADNNEGADGVG
SSSGNWHCDSQWLGDRVITTSTRTWALPTYNNHLYKQISNSTSGGSSNDNAYFGYST
PWGYFDFNRFHCHFSPRDWQRLINNNWGFRPKRLNFKLFNIQVKEVTDNNGVKTIA
NNLTSTVQVFTDSDYQLPYVLGSAHEGCLPPFPADVFMIPQYGYLTLNDGSQAVGRS
SFYCLEYFPSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSEFAWPGA
SSWALNGRNSLMNPGPAMASHKEGEDRFFPLSGSLIFGKQGTGRDNVDADKVMITN
EEEIKTTNPVATESYGQVATNHQSAQAQAQTGWVQNQGILPGMVWQDRDVYLQGP
IWAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLT
RNL >AAVrh.10 capsid protein amino acid sequence (SEQ ID NO: 7)
MAADGYLPDWLEDNLSEGIREWWDLKPGAPKPKANQQKQDDGRGLVLPGYKYLG
PFNGLDKGEPVNAADAAALEHDKAYDQQLKAGDNPYLRYNHADAEFQERLQEDTS
FGGNLGRAVFQAKKRVLEPLGLVEEGAKTAPGKKRPVEPSPQRSPDSSTGIGKKGQQ
PAKKRLNFGQTGDSESVPDPQPIGEPPAGPSGLGSGTMAAGGGAPMADNNEGADGV
GSSSGNWHCDSTWLGDRVITTSTRTWALPTYNNHLYKQISNGTSGGSTNDNTYFGY
STPWGYFDFNRFHCHFSPRDWQRLINNNWGFRPKRLNFKLFNIQVKEVTQNEGTKTI
ANNLTSTIQVFTDSEYQLPYVLGSAHQGCLPPFPADVFMIPQYGYLTLNNGSQAVGR
SSFYCLEYFPSQMLRTGNNFEFSYQFEDVPFHSSYAHSQSLDRLMNPLIDQYLYYLSR
TQSTGGTAGTQQLLFSQAGPNNMSAQAKNWLPGPCYRQQRVSTTLSQNNNSNFAW
TGATKYHLNGRDSLVNPGVAMATHKDDEERFFPSSGVLMFGKQGAGKDNVDYSSV
MLTSEEEIKTTNPVATEQYGVVADNLQQQNAAPIVGAVNSQGALPGMVWQNRDVY
LQGPIWAKIPHTDGNFHPSPLMGGFGLKHPPPQILIKNTPVPADPPTTFSQAKLASFIT
QYSTGQVSVEIEWELQKENSKRWNPEIQYTSNYYKSTNVDFAVNTDGTYSEPRPIGT
RYLTRNL >AAV5 capsid protein nucleic acid sequence (SEQ ID NO: 8)
ATGTCTTTTGTTGATCACCCTCCAGATTGGTTGGAAGAAGTTGGTGAAGGTCTTC
GCGAGTTTTTGGGCCTTGAAGCGGGCCCACCGAAACCAAAACCCAATCAGCAGC
ATCAAGATCAAGCCCGTGGTCTTGTGCTGCCTGGTTATAACTATCTCGGACCCGG
AAACGGTCTCGATCGAGGAGAGCCTGTCAACAGGGCAGACGAGGTCGCGCGAGA
GCACGACATCTCGTACAACGAGCAGCTTGAGGCGGGAGACAACCCCTACCTCAA
GTACAACCACGCGGACGCCGAGTTTCAGGAGAAGCTCGCCGACGACACATCCTT
CGGGGGAAACCTCGGAAAGGCAGTCTTTCAGGCCAAGAAAAGGGTTCTCGAACC
TTTTGGCCTGGTTGAAGAGGGTGCTAAGACGGCCCCTACCGGAAAGCGGATAGA
CGACCACTTTCCAAAAAGAAAGAAGGCCCGGACCGAAGAGGACTCCAAGCCTTC
CACCTCGTCAGACGCCGAAGCTGGACCCAGCGGATCCCAGCAGCTGCAAATCCC
AGCCCAACCAGCCTCAAGTTTGGGAGCTGATACAATGTCTGCGGGAGGTGGCGG
CCCATTGGGCGACAATAACCAAGGTGCCGATGGAGTGGGCAATGCCTCGGGAGA
TTGGCATTGCGATTCCACGTGGATGGGGGACAGAGTCGTCACCAAGTCCACCCG
AACCTGGGTGCTGCCCAGCTACAACAACCACCAGTACCGAGAGATCAAAAGCGG
CTCCGTCGACGGAAGCAACGCCAACGCCTACTTTGGATACAGCACCCCCTGGGG
GTACTTTGACTTTAACCGCTTCCACAGCCACTGGAGCCCCCGAGACTGGCAAAGA
CTCATCAACAACTACTGGGGCTTCAGACCCCGGTCCCTCAGAGTCAAAATCTTCA
ACATTCAAGTCAAAGAGGTCACGGTGCAGGACTCCACCACCACCATCGCCAACA
ACCTCACCTCCACCGTCCAAGTGTTTACGGACGACGAGTACCAGCTGCCCTACGT
CGTCGGCAACGGGACCGAGGGATGCCTGCCGGCCTTCCCTCCGCAGGTCTTTACG
CTGCCGCAGTACGGTTACGCGACGCTGAACCGCGACAACACAGAAAATCCCACC
GAGAGGAGCAGCTTCTTCTGCCTAGAGTACTTTCCCAGCAAGATGCTGAGAACG
GGCAACAACTTTGAGTTTACCTACAACTTTGAGGAGGTGCCCTTCCACTCCAGCT
TCGCTCCCAGTCAGAACCTCTTCAAGCTGGCCAACCCGCTGGTGGACCAGTACTT
GTACCGCTTCGTGAGCACAAATAACACTGGCGGAGTCCAGTTCAACAAGAACCT
GGCCGGGAGATACGCCAACACCTACAAAAACTGGTTCCCGGGGCCCATGGGCCG
AACCCAGGGCTGGAACCTGGGCTCCGGGGTCAACCGCGCCAGTGTCAGCGCCTT
CGCCACGACCAATAGGATGGAGCTCGAGGGCGCGAGTTACCAGGTGCCCCCGCA
GCCGAACGGCATGACCAACAACCTCCAGGGCAGCAACACCTATGCCCTGGAGAA
CACTATGATCTTCAACAGCCAGCCGGCGAACCCGGGCACCACCGCCACGTACCTC
GAGGGCAACATGCTCATCACCAGCGAGAGCGAGACGCAGCCGGTGAACCGCGTG
GCGTACAACGTCGGCGGGCAGATGGCCACCAACAACCAGAGCTCCACCACTGCC
CCCGCGACCGGCACGTACAACCTCCAGGAAATCGTGCCCGGCAGCGTGTGGATG
GAGAGGGACGTGTACCTCCAAGGACCCATCTGGGCCAAGATCCCAGAGACGGGG
GCGCACTTTCACCCCTCTCCGGCCATGGGCGGATTCGGACTCAAACACCCACCGC
CCATGATGCTCATCAAGAACACGCCTGTGCCCGGAAATATCACCAGCTTCTCGGA
CGTGCCCGTCAGCAGCTTCATCACCCAGTACAGCACCGGGCAGGTCACCGTGGA
GATGGAGTGGGAGCTCAAGAAGGAAAACTCCAAGAGGTGGAACCCAGAGATCC
AGTACACAAACAACTACAACGACCCCCAGTTTGTGGACTTTGCCCCGGACAGCA
CCGGGGAATACAGAACCACCAGACCTATCGGAACCCGATACCTTACCCGACCCC
TT -continued

| Sequences |
|---|

>AAV6 capsid nucleic acid sequence (SEQ ID NO: 9)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGATGCAGCGGCCC
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGAGGGTTCTCG
AACCTTTTGGTCTGGTTGAGGAAGGTGCTAAGACGGCTCCTGGAAAGAAACGTC
CGGTAGAGCAGTCGCCACAAGAGCCAGACTCCTCCTCGGGCATTGGCAAGACAG
GCCAGCAGCCCGCTAAAAAGAGACTCAATTTTGGTCAGACTGGCGACTCAGAGT
CAGTCCCCGACCCACAACCTCTCGGAGAACCTCCAGCAACCCCCGCTGCTGTGGG
ACCTACTACAATGGCTTCAGGCGGTGGCGCACCAATGGCAGACAATAACGAAGG
CGCCGACGGAGTGGGTAATGCCTCAGGAAATTGGCATTGCGATTCCACATGGCT
GGGCGACAGAGTCATCACCACCAGCACCCGAACATGGGCCTTGCCCACCTATAA
CAACCACCTCTACAAGCAAATCTCCAGTGCTTCAACGGGGGCCAGCAACGACAA
CCACTACTTCGGCTACAGCACCCCCTGGGGGTATTTTGATTTCAACAGATTCCAC
TGCCATTTCTCACCACGTGACTGGCAGCGACTCATCAACAACAATTGGGGATTCC
GGCCCAAGAGACTCAACTTCAAGCTCTTCAACATCCAAGTCAAGGAGGTCACGA
CGAATGATGGCGTCACGACCATCGCTAATAACCTTACCAGCACGGTTCAAGTCTT
CTCGGACTCGGAGTACCAGTTGCCGTACGTCCTCGGCTCTGCGCACCAGGGCTGC
CTCCCTCCGTTCCCGGCGGACGTGTTCATGATTCCGCAGTACGGCTACCTAACGC
TCAACAATGGCAGCCAGGCAGTGGGACGGTCATCCTTTTACTGCCTGGAATATTT
CCCATCGCAGATGCTGAGAACGGGCAATAACTTTACCTTCAGCTACACCTTCGAG
GACGTGCCTTTCCACAGCAGCTACGCGCACAGCCAGAGCCTGGACCGGCTGATG
AATCCTCTCATCGACCAGTACCTGTATTACCTGAACAGAACTCAGAATCAGTCCG
GAAGTGCCCAAAACAAGGACTTGCTGTTTAGCCGGGGGTCTCCAGCTGGCATGTC
TGTTCAGCCCAAAAACTGGCTACCTGGACCCTGTTACCGGCAGCAGCGCGTTTCT
AAAACAAAAACAGACAACAACAACAGCAACTTTACCTGGACTGGTGCTTCAAAA
TATAACCTTAATGGGCGTGAATCTATAATCAACCCTGGCACTGCTATGGCCTCAC
ACAAAGACGACAAAGACAAGTTCTTTCCCATGAGCGGTGTCATGATTTTTGGAAA
GGAGAGCGCCGGAGCTTCAAACACTGCATTGGACAATGTCATGATCACAGACGA
AGAGGAAATCAAAGCCACTAACCCCGTGGCCACCGAAAGATTTGGGACTGTGGC
AGTCAATCTCCAGAGCAGCAGCACAGACCCTGCGACCGGAGATGTGCATGTTAT
GGGAGCCTTACCTGGAATGGTGTGGCAAGACAGAGCGTATACCTGCAGGGTCC
TATTTGGGCCAAAATTCCTCACACGGATGGACACTTTCACCCGTCTCCTCTCATG
GGCGGCTTTGGACTTAAGCACCCGCCTCCTCAGATCCTCATCAAAAACACGCCTG
TTCCTGCGAATCCTCCGGCAGAGTTTTCGGCTACAAAGTTTGCTTCATTCATCACC
CAGTATTCCACAGGACAAGTGAGCGTGGAGATTGAATGGGAGCTGCAGAAGAA
AACAGCAAACGCTGGAATCCCGAAGTGCAGTATACATCTAACTATGCAAAATCT
GCCAACGTTGATTTCACTGTGGACAACAATGGACTTTATACTGAGCCTCGCCCCA
TTGGCACCCGTTACCTCACCCGTCCCCTG >AAV6.2 capsid protein nucleic acid sequence (SEQ ID NO: 10)
ATGGCTGCCGATGGTTATCTTCCAGATTGGCTCGAGGACAACCTCTCTGAGGGCA
TTCGCGAGTGGTGGGACTTGAAACCTGGAGCCCCGAAACCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGATGCAGCGGCCC
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CTTTTGGGGGCAACCTCGGGCGAGCAGTCTTCCAGGCCAAGAAGAGGGTTCTCG
AACCTCTTGGTCTGGTTGAGGAAGGTGCTAAGACGGCTCCTGGAAAGAAACGTC
CGGTAGAGCAGTCGCCACAAGAGCCAGACTCCTCCTCGGGCATTGGCAAGACAG
GCCAGCAGCCCGCTAAAAAGAGACTCAATTTTGGTCAGACTGGCGACTCAGAGT
CAGTCCCCGACCCACAACCTCTCGGAGAACCTCCAGCAACCCCCGCTGCTGTGGG
ACCTACTACAATGGCTTCAGGCGGTGGCGCACCAATGGCAGACAATAACGAAGG
CGCCGACGGAGTGGGTAATGCCTCAGGAAATTGGCATTGCGATTCCACATGGCT
GGGCGACAGAGTCATCACCACCAGCACCCGAACATGGGCCTTGCCCACCTATAA
CAACCACCTCTACAAGCAAATCTCCAGTGCTTCAACGGGGGCCAGCAACGACAA
CCACTACTTCGGCTACAGCACCCCCTGGGGGTATTTTGATTTCAACAGATTCCAC
TGCCATTTCTCACCACGTGACTGGCAGCGACTCATCAACAACAATTGGGGATTCC
GGCCCAAGAGACTCAACTTCAAGCTCTTCAACATCCAAGTCAAGGAGGTCACGA
CGAATGATGGCGTCACGACCATCGCTAATAACCTTACCAGCACGGTTCAAGTCTT
CTCGGACTCGGAGTACCAGTTGCCGTACGTCCTCGGCTCTGCGCACCAGGGCTGC
CTCCCTCCGTTCCCGGCGGACGTGTTCATGATTCCGCAGTACGGCTACCTAACGC
TCAACAATGGCAGCCAGGCAGTGGGACGGTCATCCTTTTACTGCCTGGAATATTT
CCCATCGCAGATGCTGAGAACGGGCAATAACTTTACCTTCAGCTACACCTTCGAG
GACGTGCCTTTCCACAGCAGCTACGCGCACAGCCAGAGCCTGGACCGGCTGATG
AATCCTCTCATCGACCAGTACCTGTATTACCTGAACAGAACTCAGAATCAGTCCG
GAAGTGCCCAAAACAAGGACTTGCTGTTTAGCCGGGGGTCTCCAGCTGGCATGTC
TGTTCAGCCCAAAAACTGGCTACCTGGACCCTGTTACCGGCAGCAGCGCGTTTCT
AAAACAAAAACAGACAACAACAACAGCAACTTTACCTGGACTGGTGCTTCAAAA
TATAACCTTAATGGGCGTGAATCTATAATCAACCCTGGCACTGCTATGGCCTCAC
ACAAAGACGACAAAGACAAGTTCTTTCCCATGAGCGGTGTCATGATTTTTGGAAA
GGAGAGCGCCGGAGCTTCAAACACTGCATTGGACAATGTCATGATCACAGACGA
AGAGGAAATCAAAGCCACTAACCCCGTGGCCACCGAAAGATTTGGGACTGTGGC

| Sequences |
| --- |
| AGTCAATCTCCAGAGCAGCAGCACAGACCCTGCGACCGGAGATGTGCATGTTAT
GGGAGCCTTACCTGGAATGGTGTGGCAAGACAGAGACGTATACCTGCAGGGTCC
TATTTGGGCAAAATTCCTCACACGGATGGACACTTTCACCCGTCTCCTCTCATG
GGCGGCTTTGGACTTAAGCACCCGCCTCCTCAGATCCTCATCAAAAACACGCCTG
TTCCTGCGAATCCTCCGGCAGAGTTTTCGGCTACAAAGTTTGCTTCATTCATCACC
CAGTATTCCACAGGACAAGTGAGCGTGGAGATTAATGGGAGCTGCAGAAAGAA
AACAGCAAACGCTGGAATCCCGAAGTGCAGTATACATCTAACTATGCAAAATCT
GCCAACGTTGATTTCACTGTGGACAACAATGGACTTTATACTGAGCCTCGCCCCA
TTGGCACCCGTTACCTCACCCGTCCCCTG >AAV7 capsid protein nucleic acid sequence (SEQ ID NO: 11)
ATGGCTGCCGATGGTTATCTTCCAGATTGGCTCGAGGACAACCTCTCTGAGGGCA
TTCGCGAGTGGTGGGACCTGAAACCTGGAGCCCCGAAACCCAAAGCCAACCAGC
AAAAGCAGGACAACGGCCGGGGTCTGGTGCTTCCTGGCTACAAGTACCTCGGAC
CCTTCAACGGACTCGACAAGGGGGAGCCCGTCAACGCGGCGGACGCAGCGGCCC
TCGAGCACGACAAGGCCTACGACCAGCAGCTCAAAGCGGGTGACAATCCGTACC
TGCGGTATAACCACGCCGACGCCGAGTTTCAGGAGCGTCTGCAAGAAGATACGT
CATTTGGGGGCAACCTCGGCAGCAGTCTTCCAGGCCAAGAAGCGGGTTCTCG
AACCTCTCGGTCTGGTTGAGGAAGGCGCTAAGACGGCTCCTGCAAAGAAGAGAC
CGGTAGAGCCGTCACCTCAGCGTTCCCCCGACTCCTCCACGGGCATCGGCAAGAA
AGGCCAGCAGCCCGCCAGAAAGAGACTCAATTTCGGTCAGACTGGCGACTCAGA
GTCAGTCCCGACCCTCAACCTCTCGGAGAACCTCCAGCAGCGCCCTCTAGTGTG
GGATCTGGTACAGTGGCTGCAGGCGGTGGCGCACCAATGGCAGACAATAACGAA
GGTGCCGACGGAGTGGGTAATGCCTCAGGAAATTGGCATTGCGATTCCACATGG
CTGGGCGACAGAGTCATTACCACCAGCACCCGAACCTGGGCCCTGCCCACCTAC
AACAACCACCTCTACAAGCAAATCTCCAGTGAAACTGCAGGTAGTACCAACGAC
AACACCTACTTCGGCTACAGCACCCCCTGGGGGTATTTTGACTTTAACAGATTCC
ACTGCCACTTCTCACCACGTGACTGGCAGCGACTCATCAACAACAACTGGGGATT
CCGGCCCAAGAAGCTGCGGTTCAAGCTCTTCAACATCCAGGTCAAGGAGGTCAC
GACGAATGACGGCGTTACGACCATCGCTAATAACCTTACCAGCACGATTCAGGT
ATTCTCGGACTCGGAATACCAGCTGCCGTACGTCCTCGGCTCTGCGCACCAGGGC
TGCCTGCCTCCGTTCCCGGCGGACGTCTTCATGATTCCTCAGTACGGCTACCTGAC
TCTCAACAATGGCAGTCAGTCTGTGGGACGTTCCTCCTTCTACTGCCTGGAGTAC
TTCCCCTCTCAGATGCTGAGAACGGGCAACAACTTTGAGTTCAGCTACAGCTTCG
AGGACGTGCCTTTCCACAGCAGCTACGCACACAGCCAGAGCCTGGACCGGCTGA
TGAATCCCCTCATCGACCAGTACTTGTACTACCTGGCAGAACACAGAGTAACCC
AGGAGGCACAGCTGGCAATCGGGAACTGCAGTTTTACCAGGGCGGGCCTTCAAC
TATGGCCGAACAAGCCAAGAATTGGTTACCTGGACCTTGCTTCCGGCAACAAAG
AGTCTCCAAAACGCTGGATCAAAACAACAACAGCAACTTTGCTTGGACTGGTGC
CACCAAATATCACCTGAACGGCAGAAACTCGTTGGTTAATCCCGGCGTCGCCATG
GCAACTCACAAGGACGACGAGGACCCGCTTTTTCCCATCCAGCGGAGTCCTGATTT
TTGGAAAAACTGGAGCAACTAACAAAACTACATTGGAAAATGTGTTAATGACAA
ATGAAGAAGAAATTCGTCCTACTAATCCTGTAGCCACGGAAGAATACGGGATAG
TCAGCAGCAACTTACAAGCGGCTAATACTGCAGCCCAGACACAAGTTGTCAACA
ACCAGGGAGCCTTACCTGGCATGGTCTGGCAGAACCGGGACGTGTACCTGCAGG
GTCCCATCTGGGCCAAGATTCCTCACACGGATGGCAACTTTCACCCGTCTCCTTT
GATGGGCGGCTTTGGACTTAAACATCCGCCTCCTCAGATCCTGATCAAGAACACT
CCCGTTCCCGCTAATCCTCCGGAGGTGTTTACTCCTGCCAAGTTTGCTTCGTTCAT
CACACAGTACAGCACCGGACAAGTCAGCGTGGAAATCGAGTGGGAGCTGCAGAA
GGAAAACAGCAAGCGCTGGAACCCGGAGATTCAGTACACCTCCAACTTTGAAAA
GCAGACTGGTGTGGACTTTGCCGTTGACAGCAGGGTGTTTACTCTGAGCCTCGC
CCTATTGGCACTCGTTACCTCACCCGTAATCTG >AAV8 capsid protein nucleic acid sequence (SEQ ID NO: 12)
ATGGCTGCCGATGGTTATCTTCCAGATTGGCTCGAGGACAACCTCTCTGAGGGCA
TTCGCGAGTGGTGGGCGCTGAAACCTGGAGCCCCGAAGCCCAAAGCCAACCAGC
AAAAGCAGGACGACGGCCGGGGTCTGGTGCTTCCTGGCTACAAGTACCTCGGAC
CCTTCAACGGACTCGACAAGGGGGAGCCCGTCAACGCGGCGGACGCAGCGGCCC
TCGAGCACGACAAGGCCTACGACCAGCAGCTGCAGGCGGGTGACAATCCGTACC
TGCGGTATAACCACGCCGACGCCGAGTTTCAGGAGCGTCTGCAAGAAGATACGT
CTTTTGGGGGCAACCTCGGGCAGCAGTCTTCCAGGCCAAGAAGCGGGTTCTCG
AACCTCTCGGTCTGGTTGAGGAAGGCGCTAAGACGGCTCCTGGAAAGAAGAGAC
CGGTAGAGCCATCACCCCAGCGTTCTCCAGACTCCTCTACGGGCATCGGCAAGAA
AGGCCAACAGCCCGCCAGAAAAAGACTCAATTTTGGTCAGACTGGCGACTCAGA
GTCAGTTCCAGACCCTCAACCTCTCGGAGAACCTCCAGCAGCGCCCTCTGGTGTG
GGACCTAATACAATGGCTGCAGGCGGTGGCGCACCAATGGCAGACAATAACGAA
GGCGCCGACGGAGTGGGTAGTTCCTCGGGAAATTGGCATTGCGATTCCACATGG
CTGGGCGACAGAGTCATCACCACCAGCACCCGAACCTGGGCCCTGCCCACCTAC
AACAACCACCTCTACAAGCAAATCTCCAACGGGACATCGGGAGGAGCCACCAAC
GACAACACCTACTTCGGCTACAGCACCCCCTGGGGGTATTTTGACTTTAACAGAT
TCCACTGCCACTTTTCACCACGTGACTGGCAGCGACTCATCAACAACAACTGGGG
ATTCCGGCCCAAGAGACTCAGCTTCAAGCTCTTCAACATCCAGGTCAAGGAGGTC
ACGCAGAATGAAGGCACCAAGACCATCGCCAATAACCTCACCAGCACCATCCAG
GTGTTTACGGACTCGGAGTACCAGCTGCCGTACGTTCTCGGCTCTGCCCACCAGG
GCTGCCTGCCTCCGTTCCCGGCGGACGTGTTCATGATTCCCCAGTACGGCTACCT
AACACTCAACAACGGTAGTCAGGCCGTGGGACGCTCCTCCTTCTACTGCCTGGAA
TACTTTCCTTCGCAGATGCTGAGAACCGGCAACAACTTCCAGTTTACTTACACCTT

```
CGAGGACGTGCCTTTCCACAGCAGCTACGCCCACAGCCAGAGCTTGGACCGGCT
GATGAATCCTCTGATTGACCAGTACCTGTACTACTTGTCTCGGACTCAAACAACA
GGAGGCACGGCAAATACGCAGACTCTGGGCTTCAGCCAAGGTGGGCCTAATACA
ATGGCCAATCAGGCAAAGAACTGGCTGCCAGGACCCTGTTACCGCCAACAACGC
GTCTCAACGACAACCGGGCAAAACAACAATAGCAACTTTGCCTGGACTGCTGGG
ACCAAATACCATCTGAATGGAAGAAATTCATTGGCTAATCCTGGCATCGCTATGG
CAACACACAAAGACGACGAGGAGCGTTTTTTTCCCAGTAACGGGATCCTGATTTT
TGGCAAACAAAATGCTGCCAGAGACAATGCGGATTACAGCGATGTCATGCTCAC
CAGCGAGGAAGAAATCAAAACCACTAACCCTGTGGCTACAGAGGAATACGGTAT
CGTGGCAGATAACTTGCAGCAGCAAAACACGGCTCCTCAAATTGGAACTGTCAA
CAGCCAGGGGGCCTTACCCGGTATGGTCTGGCAGAACCGGGACGTGTACCTGCA
GGGTCCCATCTGGGCCAAGATTCCTCACACGGACGGCAACTTCCACCCGTCTCCG
CTGATGGGCGGCTTTGGCCTGAAACATCCTCCGCCTCAGATCCTGATCAAGAACA
CGCCTGTACCTGCGGATCCTCCGACCACCTTCAACCAGTCAAAGCTGAACTCTTT
CATCACGCAATACAGCACCGGACAGGTCAGCGTGGAAATTGAATGGGAGCTGCA
GAAGGAAAACAGCAAGCGCTGGAACCCCGAGATCCAGTACACCTCCAACTACTA
CAAATCTACAAGTGTGGACTTTGCTGTTAATACAGAAGGCGTGTACTCTGAACCC
CGCCCCATTGGCACCCGTTACCTCACCCGTAATCTG

>AAV9 capsid protein nucleic acid sequence (SEQ ID NO: 13)
ATGGCTGCCGATGGTTATCTTCCAGATTGGCTCGAGGACAACCTTAGTGAAGGAA
TTCGCGAGTGGTGGGCTTTGAAACCTGGAGCCCCTCAACCCAAGGCAAATCAAC
AACATCAAGACAACGCTCGAGGTCTTGTGCTTCCGGGTTACAAATACCTTGGACC
CGGCAACGGACTCGACAAGGGGGAGCCGGTCAACGCAGCAGACGCGGCGGCCC
TCGAGCACGACAAGGCCTACGACCAGCAGCTCAAGGCCGGAGACAACCCGTACC
TCAAGTACAACCACGCCGACGCCGAGTTCCAGGAGCGGCTCAAAGAAGATACGT
CTTTTGGGGGCAACCTCGGGCGAGCAGTCTTCCAGGCCAAAAAGAGGCTTCTTGA
ACCTCTTGGTCTGGTTGAGGAAGCGGCTAAGACGGCTCCTGGAAAGAAGAGGCC
TGTAGAGCAGTCTCCTCAGGAACCGGACTCCTCCGCGGGTATTGGCAAATCGGGT
GCACAGCCCGCTAAAAAGAGACTCAATTTCGGTCAGACTGGCGACACAGAGTCA
GTCCCAGACCCTCAACCAATCGGAGAACCTCCCGCAGCCCCCTCAGGTGTGGGAT
CTCTTACAATGGCTTCAGGTGGTGGCGCACCAGTGGCAGACAATAACGAAGGTG
CCGATGGAGTGGGTAGTTCCTCGGGAAATTGGCATTGCGATTCCCAATGGCTGGG
GGACAGAGTCATCACCACCAGCACCCGAACCTGGGCCCTGCCCACCTACAACAA
TCACCTCTACAAGCAAATCTCCAACAGCACATCTGGAGGATCTTCAAATGACAAC
GCCTACTTCGGCTACAGCACCCCCTGGGGGTATTTTGACTTCAACAGATTCCACT
GCCACTTCTCACCACGTGACTGGCAGCGACTCATCAACAACAACTGGGGATTCCG
GCCTAAGCGACTCAACTTCAAGCTCTTCAACATTCAGGTCAAAGAGGTTACGGAC
AACAATGGAGTCAAGACCATCGCCAATAACCTTACCAGCACGGTCCAGGTCTTC
ACGGACTCAGAGTATCAGCTCCCGTACGTGCTCGGGTCGGCTCACGAGGGCTGC
CTCCCGCCGTTCCCAGCGGACGTTTTCATGATTCCTCAGTACGGGTATCTGACGCT
TAATGATGGAAGCCAGGCCGTGGGTCGTTCGTCCTTTTACTGCCTGGAATATTTCC
CGTCGCAAATGCTAAGAACGGGTAACAACTTCCAGTTCAGCTACGAGTTTGAGA
ACGTACCTTTCCATAGCAGCTACGCTCACAGCCAAAGCCTGGACCGACTAATGAA
TCCACTCATCGACCAATACTTGTACTATCTCTCAAAGACTATTAACGGTTCTGGA
CAGAATCAACAAACGCTAAAATTCAGTGTGGCCGGACCCAGCAACATGGCTGTC
CAGGGAAGAAACTACATACCTGGACCCAGCTACCGACAACAACGTGTCTCAACC
ACTGTGACTCAAAACAACAACAGCGAATTTGCTTGGCCTGGAGCTTCTTCTTGGG
CTCTCAATGGACGTAATAGCTTGATGAATCCTGGACCTGCTATGGCCAGCCACAA
AGAAGGAGAGGACCGTTTCTTTCCTTTGTCTGGATCTTTAATTTTTGGCAAACAA
GGAACTGGAAGAGACAACGTGGATGCGGACAAAGTCATGATAACCAACGAAGA
AGAAATTAAAACTACTAACCCGGTAGCAACGGAGTCCTATGGACAAGTGGCCAC
AAACCACCAGAGTGCCCAAGCACAGGCGCAGACCGGCTGGGTTCAAAACCAAGG
AATACTTCCGGGTATGGTTTGGCAGGACAGAGATGTGTACCTGCAAGGACCCATT
TGGGCCAAAATTCCTCACACGGACGGCAACTTTCACCCTTCTCCGCTGATGGGAG
GGTTTGGAATGAAGCACCCGCCTCCTCAGATCCTCATCAAAAACACACCTGTACC
TGCGGATCCTCCAACGGCCTTCAACAAGGACAAGCTGAACTCTTTCATCACCCAG
TATTCTACTGGCCAAGTCAGCGTGGAGATCGAGTGGGAGCTGCAGAAGGAAAAC
AGCAAGCGCTGGAACCCGGAGATCCAGTACACTTCCAACTATTACAAGTCTAAT
AATGTTGAATTTGCTGTTAATACTGAAGGTGTATATAGTGAACCCCGCCCCATTG
GCACCAGATACCTGACTCGTAATCTG >AAVrh.10 capsid protein nucleic acid sequence (SEQ ID NO: 14)
TCGAGGACAACCTCTCTGAGGGCATTCGCGAGTGGTGGGACTTGAAACCTGGAG
CCCCGAAACCCAAAGCCAACCAGCAAAAGCAGGACGACGGCCGGGGTCTGGTGC
TTCCTGGCTACAAGTACCTCGGACCCTTCAACGGACTCGACAAGGGGGAGCCCGT
CAACGCGGCGGACGCAGCGGCCCTCGAGCACGACAAGGCCTACGACCAGCAGCT
CAAAGCGGGTGACAATCCGTACCTGCGGTATAACCACGCCGACGCCGAGTTTCA
GGAGCGTCTGCAAGAAGATACGTCTTTTGGGGGCAACCTCGGGCGAGCAGTCTT
CCAGGCCAAGAAGCGGGTTCTCGAACCTCTCGGTCTGGTTGAGGAAGGCGCTAA
GACGGCTCCTGGAAAGAAGAGACCGGTAGAGCCATCACCCCAGCGTTCTCCAGA
CTCCTCTACGGGCATCGGCAAGAAAGGCCAGCAGCCCGCGAAAAAGAGACTCAA
CTTTGGGCAGACTGGCGACTCAGAGTCAGTGCCCGACCCTCAACCAATCGGAGA
ACCCCCCGCAGGCCCCTCTGGTCTGGGATCTGGTACAATGGCTGCAGGCGGTGGC
GCTCCAATGGCAGACAATAACGAAGGCGCCGACGGAGTGGGTAGTTCCTCAGGA
AATTGGCATTGCGATTCCACATGGCTGGGCGACAGAGTCATCACCACCAGCACCC
GAACCTGGGCCCTCCCCACCTACAACAACCACCTCTACAAGCAAATCTCCAACGG
```

| Sequences |
|---|
| GACTTCGGGAGGAAGCACCAACGACAACACCTACTTCGGCTACAGCACCCCCTG
GGGGTATTTTGACTTTAACAGATTCCACTGCCACTTCTCACCACGTGACTGGCAG
CGACTCATCAACAACAACTGGGGATTCCGGCCCAAGAGACTCAACTTCAAGCTCT
TCAACATCCAGGTCAAGGAGGTCACGCAGAATGAAGGCACCAAGACCATCGCCA
ATAACCTTACCAGCACGATTCAGGTCTTTACGGACTCGGAATACCAGCTCCCGTA
CGTCCTCGGCTCTGCGCACCAGGGCTGCCTGCCTCCGTTCCCGGCGGACGTCTTC
ATGATTCCTCAGTACGGGTACCTGACTCTGAACAATGGCAGTCAGGCCGTGGGCC
GTTCCTCCTTCTACTGCCTGGAGTACTTTCCTTCTCAAATGCTGAGAACGGGCAAC
AACTTTGAGTTCAGCTACCAGTTTGAGGACGTGCCTTTTCACAGCAGCTACGCGC
ACAGCCAAAGCCTGGACCGGCTGATGAACCCCCTCATCGACCAGTACCTGTACTA
CCTGTCTCGGACTCAGTCCACGGGAGGTACCGCAGGAACTCAGCAGTTGCTATTT
TCTCAGGCCGGGCCTAATAACATGTCGGCTCAGGCCAAAAACTGGCTACCCGGG
CCCTGCTACCGGCAGCAACGCGTCTCCACGACACTGTCGCAAAATAACAACAGC
AACTTTGCCTGGACCGGTGCCACCAAGTATCATCTGAATGGCAGAGACTCTCTGG
TAAATCCCGGTGTCGCTATGGCAACCCACAAGGACGACGAAGAGCGATTTTTCC
GTCCAGCGGAGTCTTAATGTTTGGGAAACAGGGAGCTGGAAAAGACAACGTGGA
CTATAGCAGCGTTATGCTAACCAGTGAGGAAGAAATTAAAACCACCAACCCAGT
GGCCACAGAACAGTACGGCGTGGTGGCCGATAACCTGCAACAGCAAAACGCCGC
TCCTATTGTAGGGGCCGTCAACAGTCAAGGAGCCTTACCTGGCATGGTCTGGCAG
AACCGGGACGTGTACCTGCAGGGTCCTATCTGGGCCAAGATTCCTCACACGGAC
GGGAAACTTTCATCCCTCGCCGCTGATGGGAGGCTTTGGACTGAAACACCCGCCTC
CTCAGATCCTGATTAAGAATACACCTGTTCCCGCGGATCCTCCAACTACCTTCAG
TCAAGCTAAGCTGGCGTCGTTCATCACGCAGTACAGCACCGGACAGGTCAGCGT
GGAAATTGAATGGGAGCTGCAGAAAGAAAACAGCAAACGCTGGAACCCAGAGA
TTCAATACACTTCCAACTACTACAAATCTACAAATGTGGACTTTGCTGTTAACAC
AGATGGCACTTATTCTGAGCCTCGCCCCATCGGCACCCGTTACCTCACCCGTAAT
CTGTAATTGCTTGTTAATCAATAAACCGGTTGATTCGTTTCAGTTGAACTTTGGTC
TCTGCGAAGGGCGAATTCGTTT |

>miR34a nucleic acid sequence (SEQ ID NO 15)
AGGAATTCTGCTGGAGGAGTGTGTCATACCTCGGTAGGGTCCACTACACATCTTT
CTCCCGCAGCCTCTCCATCTTCCTGTGACTGCGGGCGCCTCAGCCTGGGCTGCC
AGCTGTGAGTAATTCTTTGGCAGTGTCTTAGCTGGTTGTTGTGAGTATTAGCTAA
GGAAGCAATCAGCAAGTATACTGCCCTAGAAGTGCTGCACATTGTTGGGCCGAG
AAGGAAAAGGTCAGAGGTCAGCAACGCCCACACCCCTGAGAGGCGCTGGACTTG
CGGAGCTGCTCGACCATACTGGTGGGTATGGGATGGCGGCCGCGTCCC >miR34a-Gluc expression construct nucleic acid sequence (SEQ ID NO: 16)
CTGCGCGCTCGCTCGCTCACTGAGGCCGCCCGGGCAAAGCCCGGGCGTCGGGCG
ACCTTTGGTCGCCCGGCCTCAGTGAGCGAGCGAGCGCGCAGAGAGGGAGTGTAG
CCATGCTCTAGGAAGATCAATTCGGTACAATTCACGCGTCGACATTGATTATTGA
CTCTGGTCGTTACATAACTTACGGTAAATGGCCCGCCTGGCTGACCGCCCAACGA
CCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAA
TGGCCCGCCTGGCATTATGCCCAGTACATGACCTTATGGGACTTTCCTACTTGGC
AGTACATCTACTCGAGGCCACGTTCTGCTTCACTCTCCCCATCTCCCCCCCCTCCC
CACCCCCAATTTTGTATTTATTTATTTTTTAATTATTTTGTGCAGCGATGGGGGCG
GGGGGGGGGGGGGGGGCGCGCGCCAGGCGGGGCGGGGCGGGGCGAGGGG
CGGGGCGGGGCGAGGCGGAGAGGTGCGGCGGCAGCCAATCAGAGCGGCGCGCT
CCGAAAGTTTCCTTTTATGGCGAGGCGGCGGCGGCGGCGGCCCTATAAAAAGCG
AAGCGCGCGGCGGGCGGGAGCGGGATCAGCCACCGCGGTGGCGGCCCTAGAGTC
GATCGAGGAACTGAAAAACCAGAAAGTTAACTGGTAAGTTTAGTCTTTTTGTCTT
TTATTTCAGGAATTCTGCTGGAGGAGTGTGTCATACCTCGGTAGGGTCCACTACA
CATCTTTCTCCCGCAGCCTCTCCATCTTCCTGTGACTGCGGGCGCCTCAGCCTGGG
CTGGCCAGCTGTGAGTAATTCTTTGGCAGTGTCTTAGCTGGTTGTTGTGAGTATTA
GCTAAGGAAGCAATCAGCAAGTATACTGCCCTAGAAGTGCTGCACATTGTTGGG
CCGAGAAGGAAAAGGTCAGAGGTCAGCAACGCCCACACCCCTGAGAGGCGCTG
GACTTGCGGAGCTGCTCGACCATACTGGTGGGTATGGGATGGCGGCCGCGTCCC
GGATCCGGTGGTGGTGCAAATCAAAGAACTGCTCCTCAGTGGATGTTGCCTTTAC
TTCTAGGCCTGTACGGAAGTGTTACTTCTGCTCTAAAAGCTGCGGAATTGTACCC
GCGGCCGATCCACCGGTCGCCACCATCTAGCATGGGAGTCAAAGTTCTGTTTGCC
CTGATCTGCATCGCTGTGGCCGAGGCCAAGCCCACCGAGAACAACGAAGACTTC
AACATCGTGGCCGTGGCCAGCAACTTCGCGACCACGGATCTCGATGCTGACCGC
GGGAAGTTGCCCGGCAAGAAGCTGCCGCTGGAGGTGCTCAAAGAGATGGAAGCC
AATGCCCGGAAAGCTGGCTGCACCAGGGCTGTCTGATCTGCCTGTCCCACATCA
AGTGCACGCCCAAGATGAAGAAGTTCATCCCAGGACGCTGCCACACCCTACGAAG
GCGACAAAGAGTCCGCACAGGGCGGCATAGGCGAGGCGATCGTCGACATTCCTG
AGATTCCTGGGTTCAAGGACTTGGAGCCCATGGAGCAGTTCATCGCACAGGTCG
ATCTGTGTGTGGACTGCACAACTGGCTGCCTCAAAGGGCTTGCCAACGTGCAGTG
TTCTGACCTGCTCAAGAAGTGGCTGCCGCAACGCTGTGCGACCTTTGCCAGCAAG
ATCCAGGGCCAGGTGGACAAGATCAAGGGGGCCGGTGGTGACTAGCTCGACGCT
GATCAGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATG
AGGAAATTGCATCGCATTGTCTGAGTAGGTGTCATTCTATTCTGGGGGGTGGGT
GGGGCAGGACAGCAAGGGGGAGGATTGGGAAGACAATTAGGTAGATAAGTAGC
ATGGCGGGTTAATCATTAACTACAAGGAACCCCTAGTGATGGAGTTGGCCACTCC -continued Sequences CTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAG

EXAMPLES

Example 1. Adeno-Associated Virus Serotype Vectors Efficiently Transduce Normal Prostate Tissue and Prostate Cancer Cells This example describes the unexpected result that certain serotypes of AAV vectors mediate highly efficient transduction in prostate tissue (e.g., mouse prostate tissue), which may be useful for performing mechanistic studies and gene therapy for prostate diseases, such as prostate cancer, in subjects such as dogs, monkeys, and humans (see, for example, Martijn C. Nawijn et al. European Urology Supplements, 7, 566-575, 2008 and Cory Abate-Shen, et al. Trends in Genetics. 18 (5):S1-S5, 2002).

It was previously shown that intraperitoneal (i.p.) injection of certain rAAV serotypes such as rAAV8 into WT mice could transduce tissues surrounding the peritoneal cavity such as the diaphragm, but prostate transduction has not been reported to the best of Applicants' knowledge. To screen for rAAV serotypes that efficiently transduce mouse prostate in vivo, i.p. injection of 12 serotypes of enhanced green fluorescent protein (EGFP)-expressing rAAV vectors was performed in WT C57BL/6 male mice, including rAAV2, 3b, 5, 6, 6.2, 7, 8, 9, rh.8, rh.10, rh.39 and rh.43.

EGFP fluorescence signal was barely observed in the prostate tissue sections three weeks after vector injection, indicating inefficient transduction. Next, the same panel of rAAV vectors was injected directly into mouse prostate. The mouse prostate is divided into anterior prostate (AP) that contains two lobes and dorsal lateral prostate (DLP) (FIG. 1). rAAV vectors were thus injected into four sites per prostate, namely the two lobes of AP and two sites of DLP (FIG. 1).

Figure 2A:
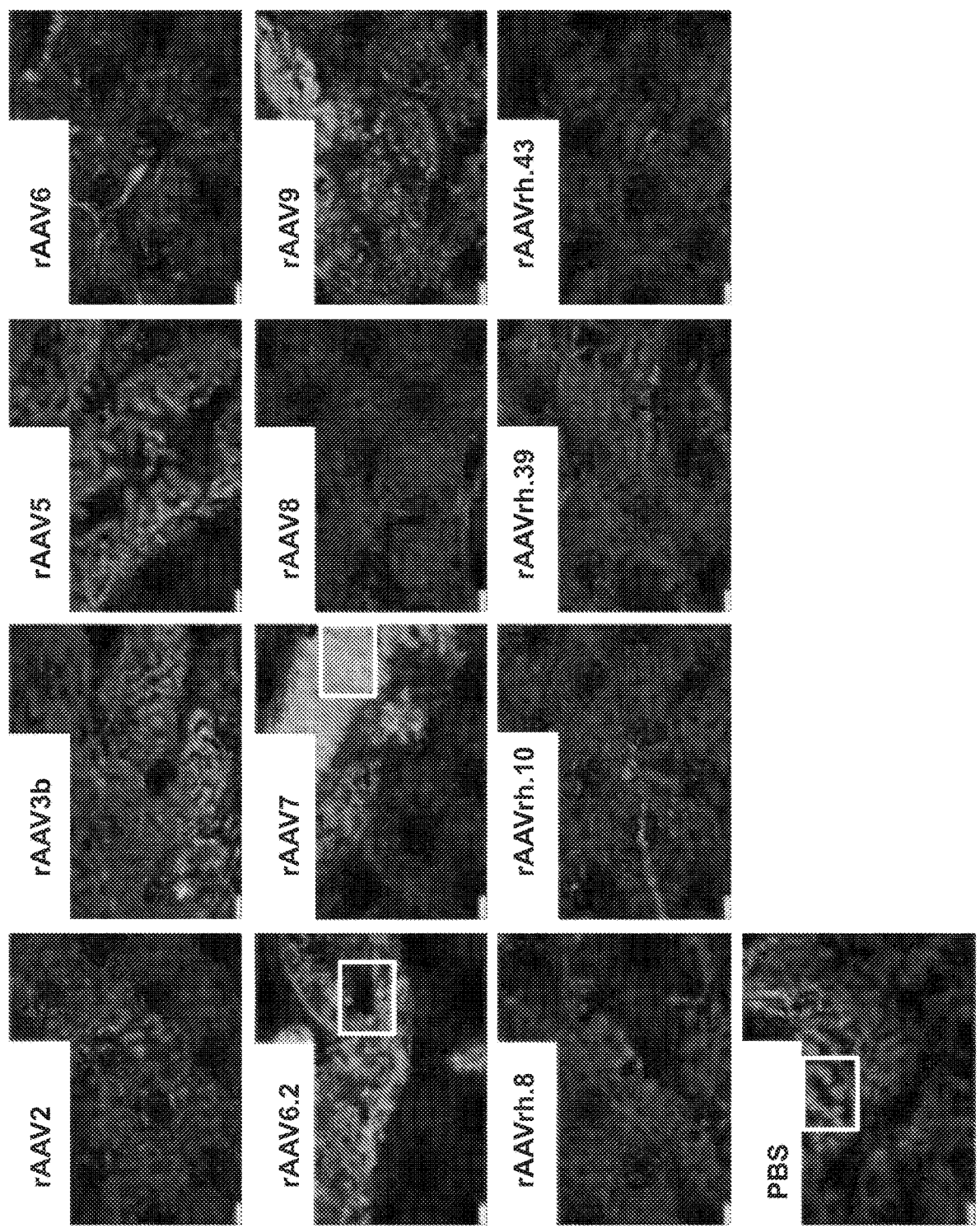
FIGS. 2A-2B show rAAV6.2, 7 and 9 efficiently transduced mouse AP following intraprostate injection.
Figure 2B:
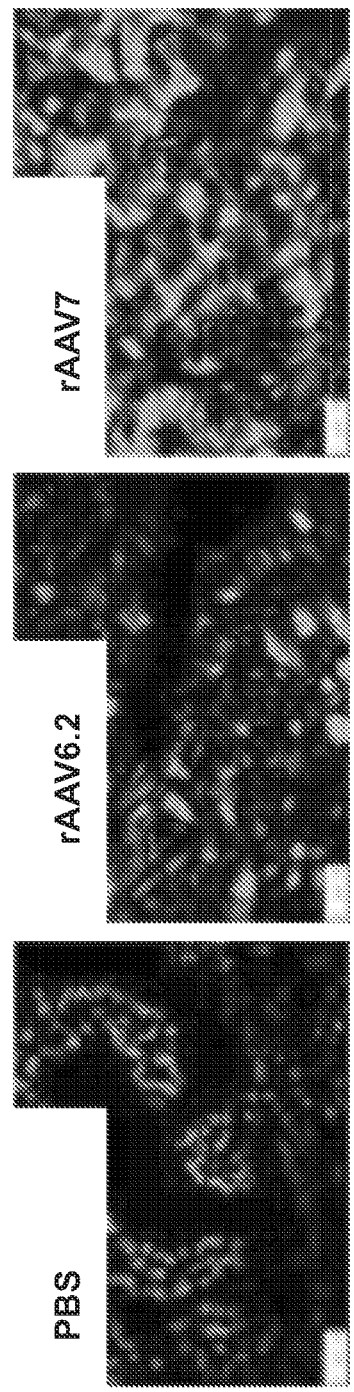
Figure 3A:
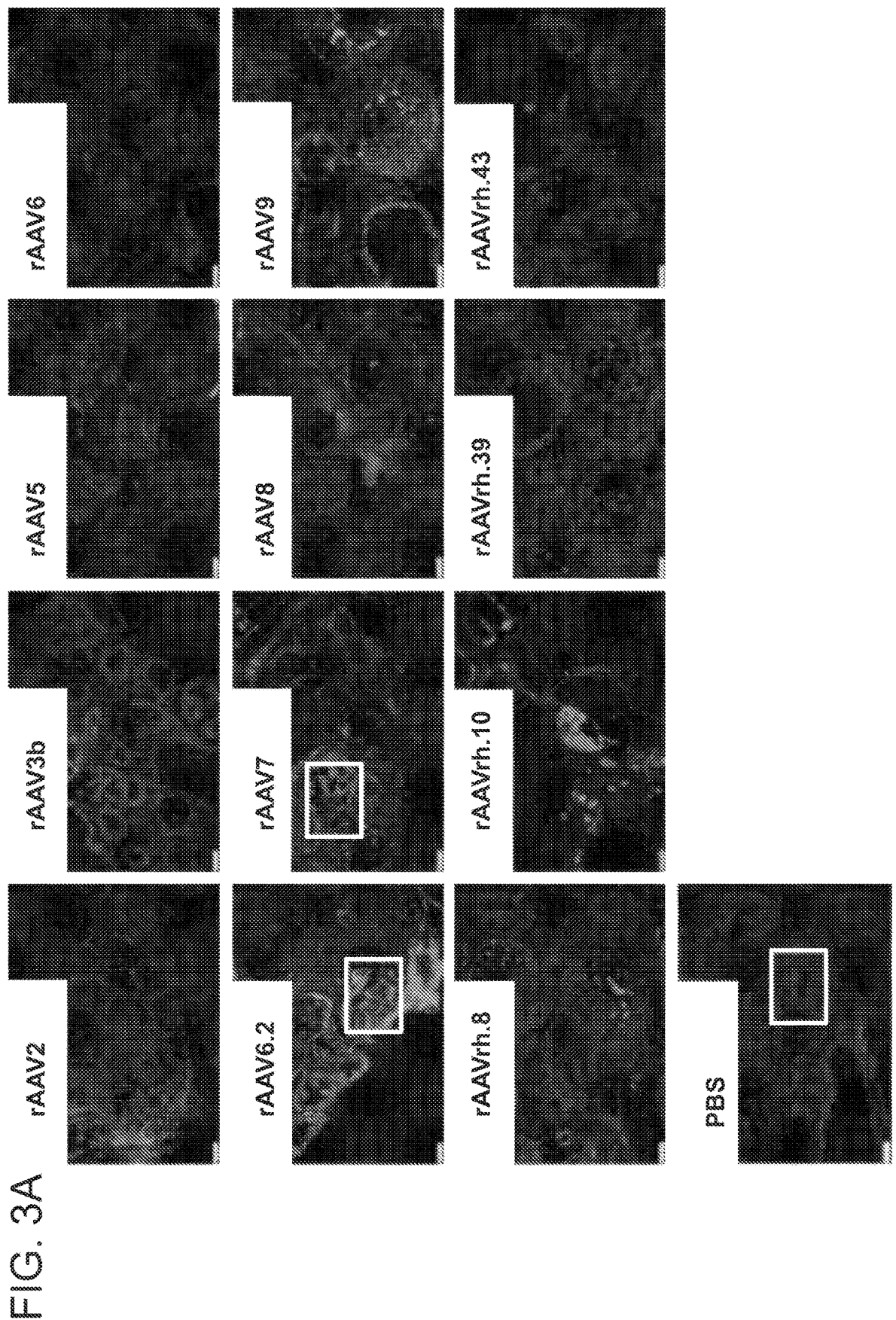
FIGS. 3A-3B show rAAV6.2, and 7 efficiently transduced mouse DLP following intraprostate injection.
Figure 3B:
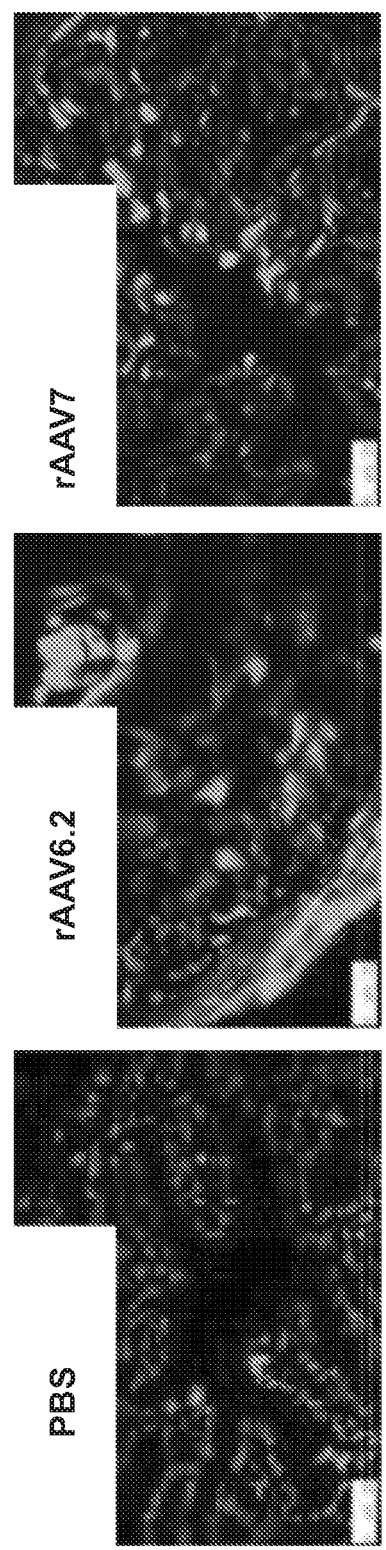
Figure 5:
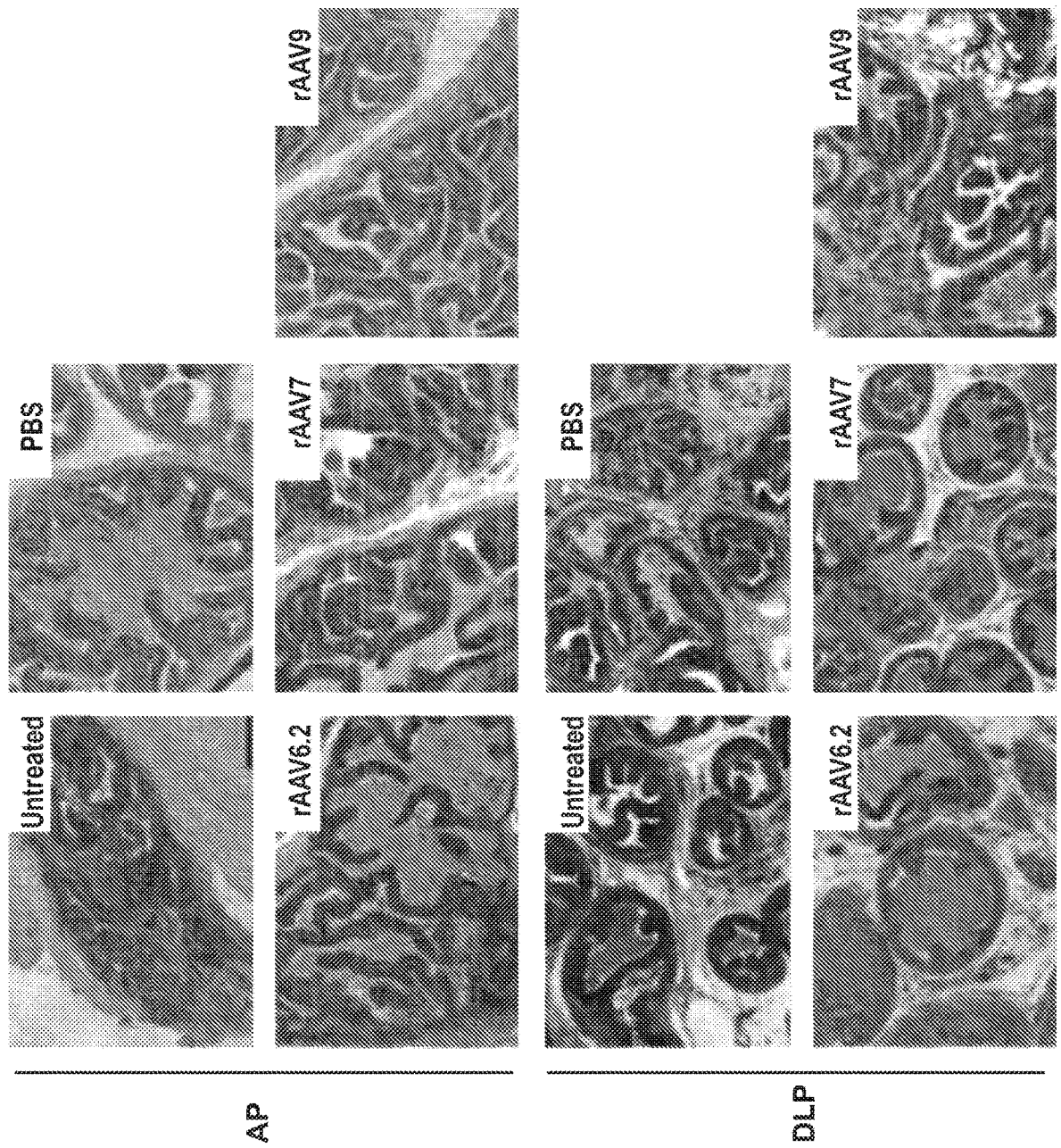
FIG. 5 shows intraprostate injection of rAAV vectors and transduction had no adverse effect on prostate histology. Representative H&E staining images of AP and DLP tissue sections collected from mice that were not treated (untreated), treated with PBS, or three rAAV serotype vectors including rAAV6.2, 7 and 9. Scale bars represent 100 microns.

Three weeks after injection, AP and DLP cryo-sections were subjected to fluorescence microscopy. It was found that rAAV6.2, rAAV7 and rAAV9 outperformed the other serotypes in transducing AP (FIGS. 2A-2B, FIG. 4A). Among these three serotypes, rAAV6.2 and rAAV7 also transduced DLP efficiently (FIGS. 3A-3B, FIG. 4A). In addition, rAAV5, rAAV8 and rAAVrh.10 transduced DLP (FIG. 3A, FIG. 4A). For the two leading serotypes that transduced both AP and DLP (rAAV6.2 and rAAV7), the vector genome biodistribution in the injected AP and DLP was determined to be approximately 10-20 rAAV genome copies per cell (FIG. 4B). Normal histology was observed by H&E staining in both AP and DLP, without indication of inflammation or other adverse effects following PBS or rAAV injection (FIG. 5). These results suggested that rAAV6.2 and rAAV7 are good candidates for efficient and safe delivery of genes of interest to mouse prostate in vivo.

Figure 6B:
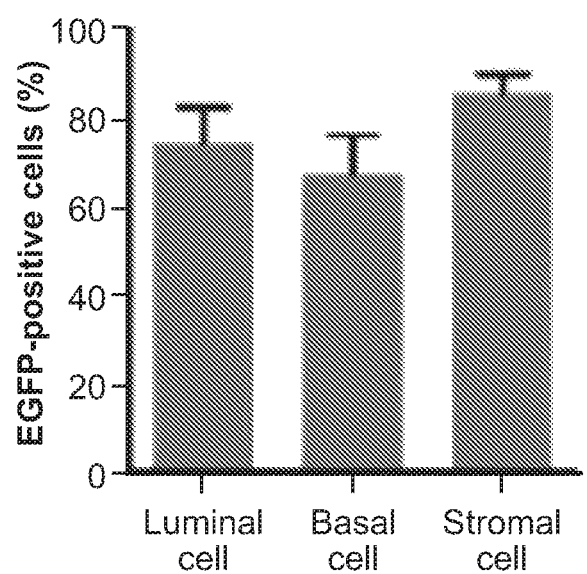

To further characterize the prostatic cell types that were transduced with rAAV6.2 and rAAV7, immunofluorescence staining of mouse AP and DLP sections was performed with antibodies against cellular markers of major prostate cell types including luminal cells (K8), basal cells (K5) and stromal cells (α-actin for smooth muscle cells). It was found that both serotypes were able to transduce the majority of the three cell types in both AP and DLP. Representative fluorescence microscopic images are shown in FIG. 6A. Quantification of EGFP-positive cells of each cell type revealed that 65-80% of luminal cells, basal cells and stromal cells could be transduced (FIG. 6B).

Example 2. rAAV-Based and Intraprostatically Delivered miR-34a Therapeutics for Efficient Inhibition of Prostate Cancer Progression Prostate cancer (PCa) is the second most common diagnosed cancer and the fifth cause of cancer-related mortality for males worldwide. At present, there is no effective treatment for PCa. Towards further understanding molecular mechanism and developing therapeutics for PCa, the role of miR34a in PCa progression was investigated.

Figure 7A:
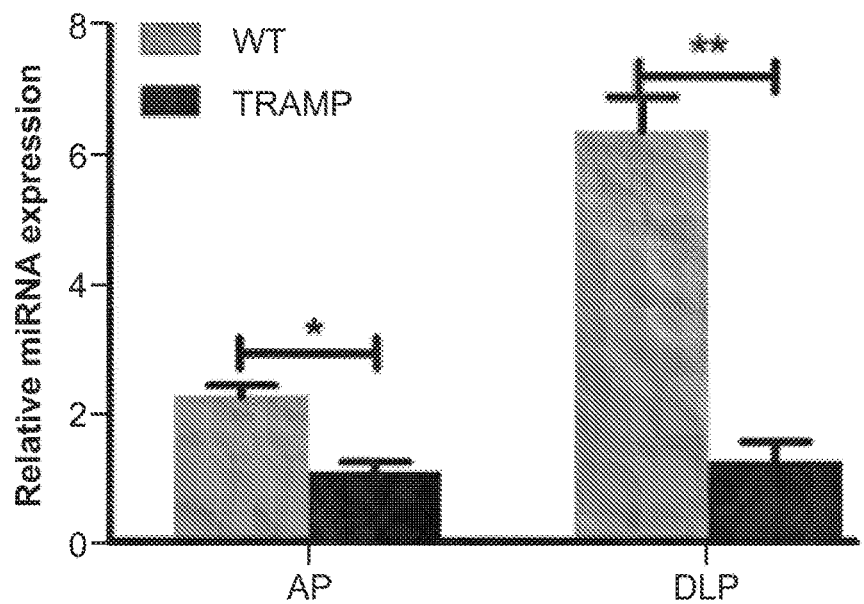
FIGS. 7A-7B show data relating to miR34a expression in prostate cancer.
Figure 7B:
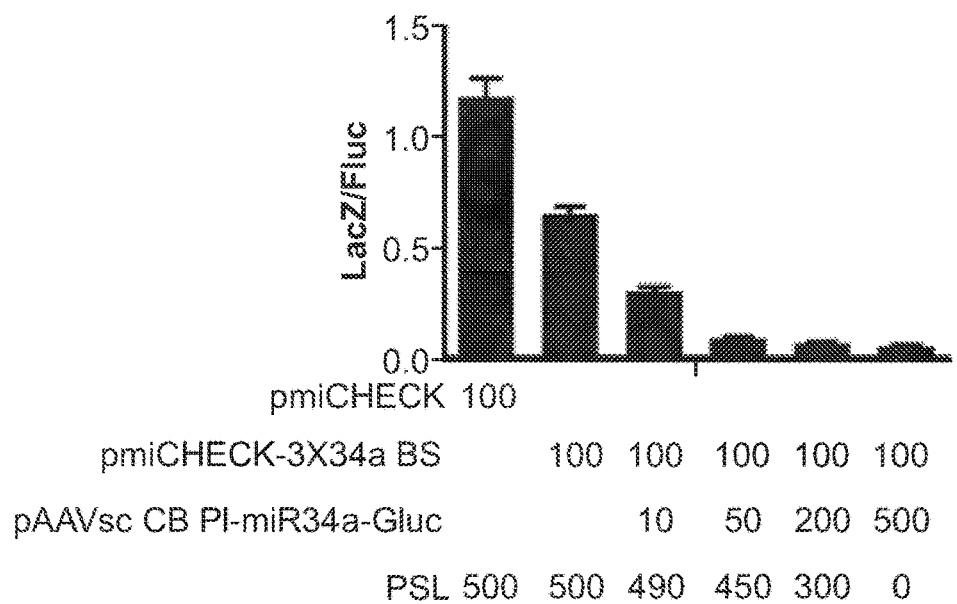
Figure 8A:
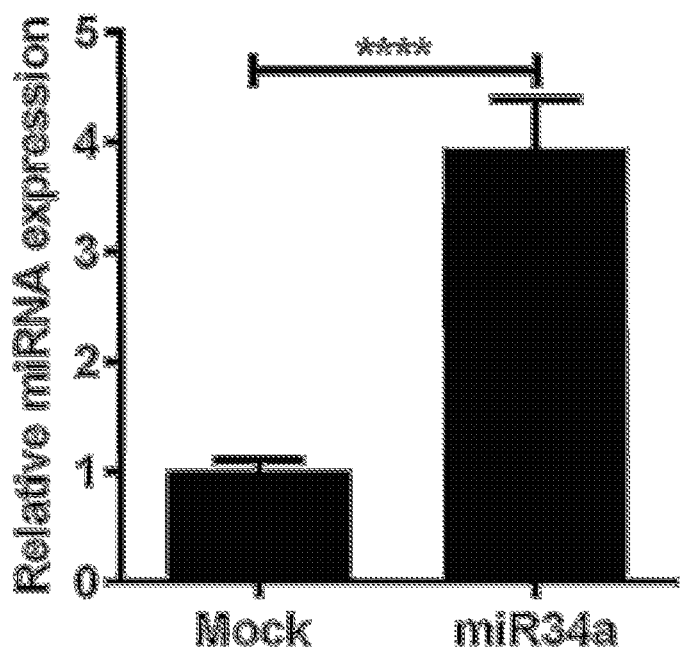
FIGS. 8A-8E show miR34a overexpression inhibits prostate cancer cell cycle.
Figure 8B:
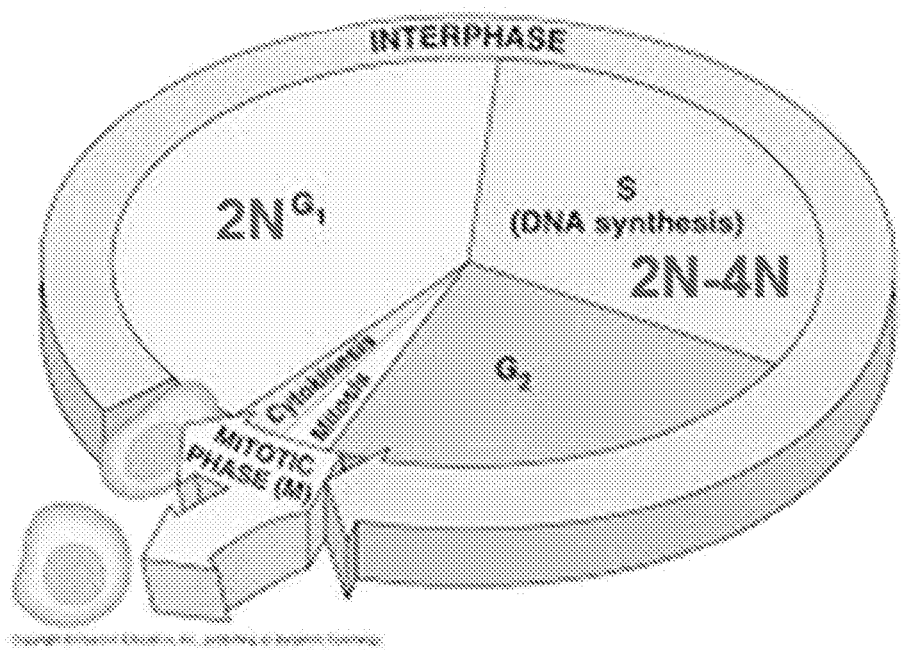
Figure 8C:
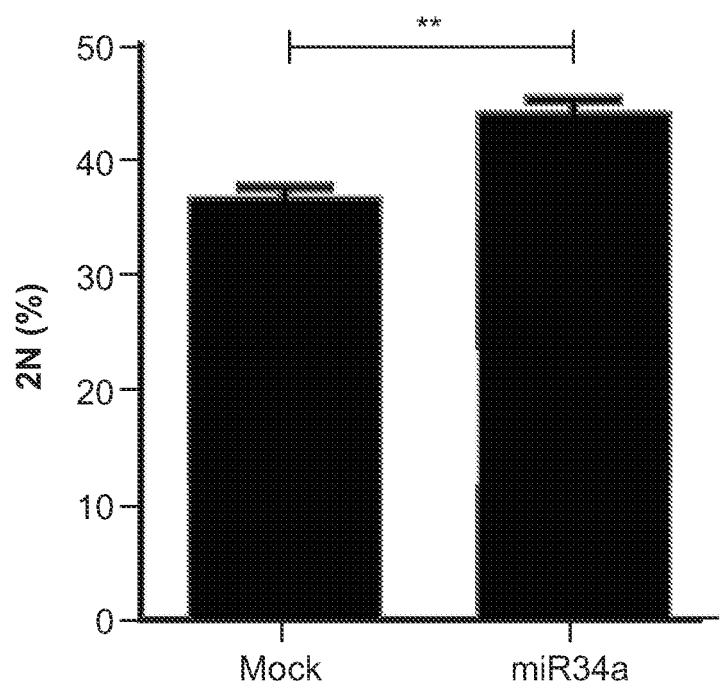
Figure 8D:
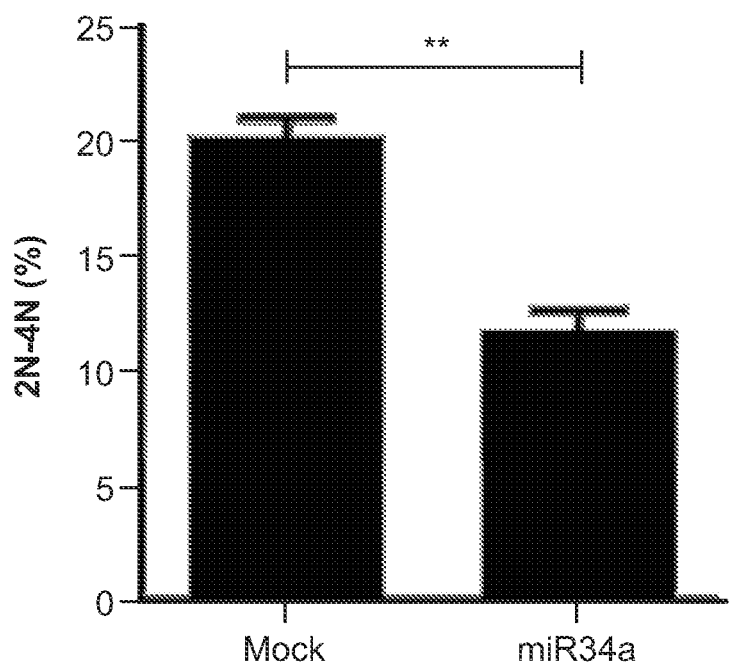
Figure 8E:
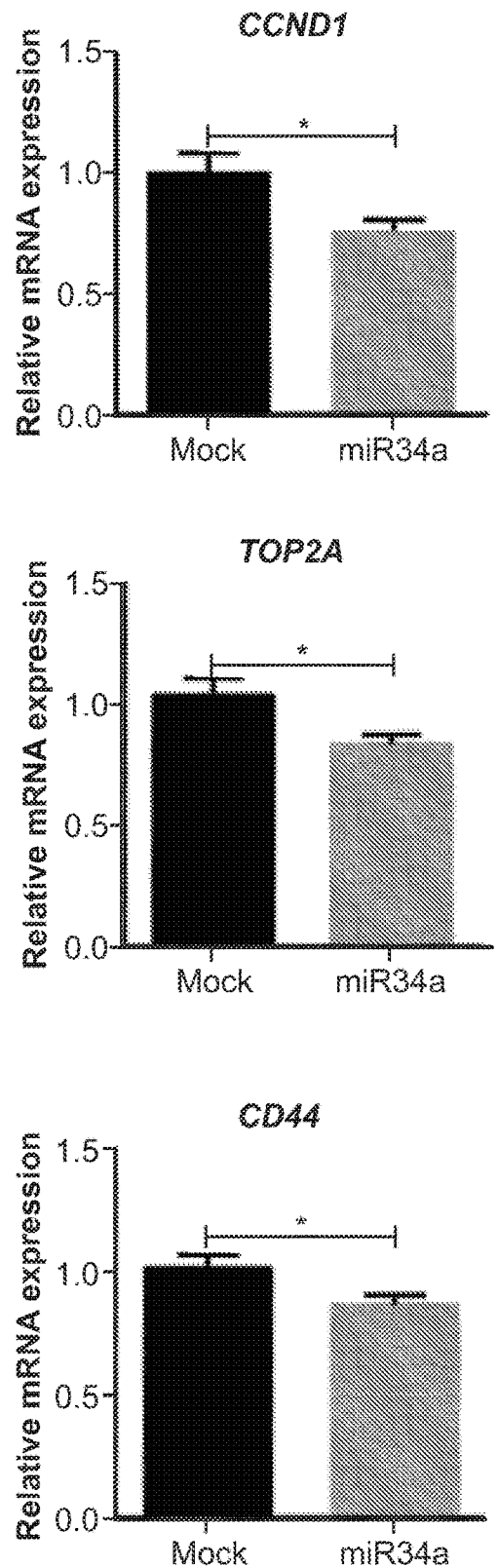
Figure 9A:
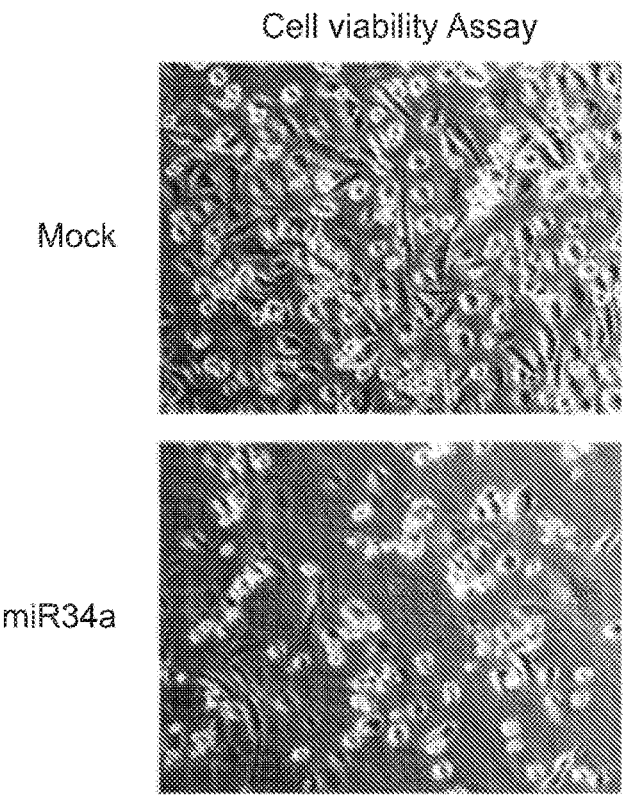
FIGS. 9A-9D show miR34a overexpression reduces cell viability and inhibits migration of PC3 prostate cancer cells.
Figure 9B:
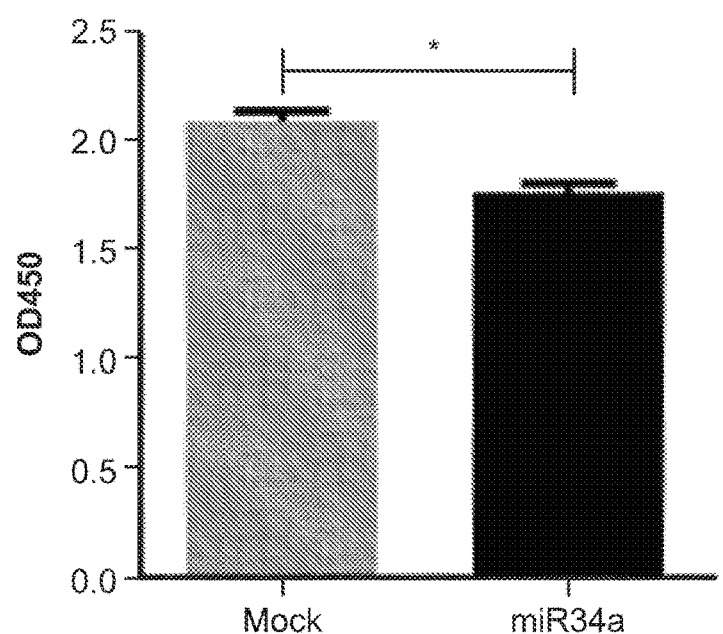
Figure 9C:
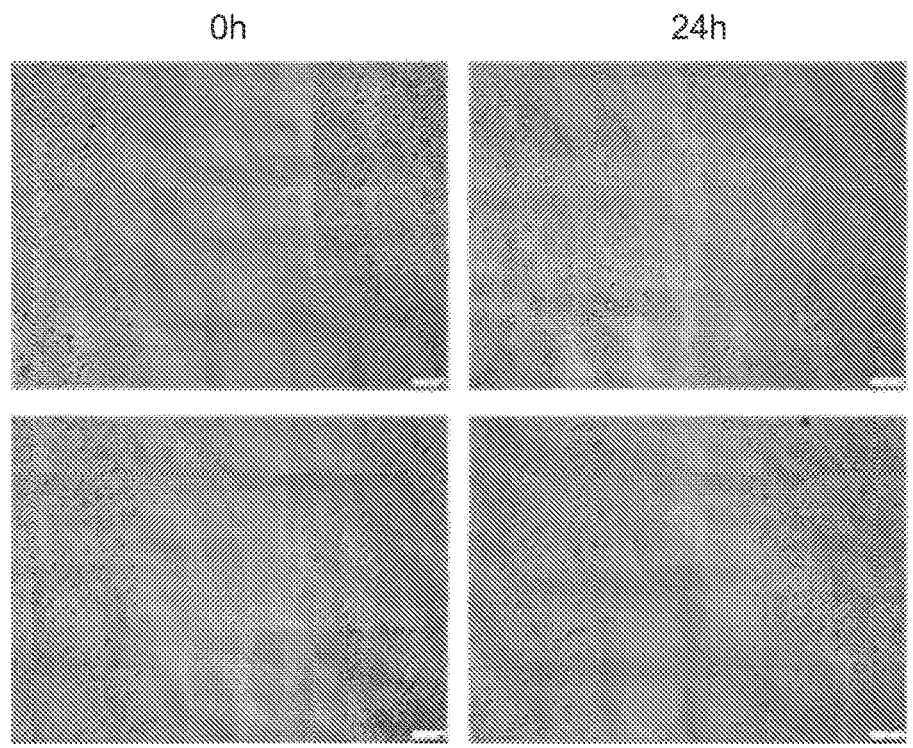
Figure 9D:
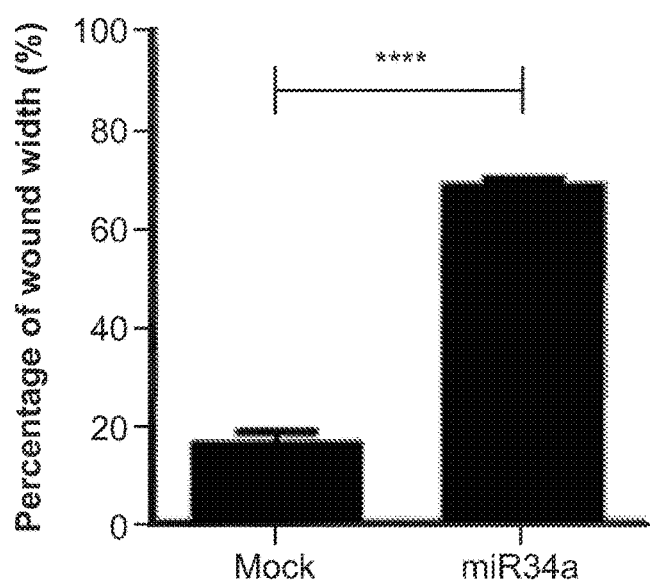

Expression of miR-34a is significantly downregulated in PCa cells. Here, downregulation of miR34a in prostate tumor from transgenic adenocarcinoma mouse prostate (TRAMP) model was examined. Relative expression of miR34a in prostate tissue of wild type and TRAMP mice was quantified by quantitative PCR (qPCR). Results demonstrate that expression of miR34a is significantly downregulated in the TRAMP mice (FIG. 7A). An rAAV-pri-miR34a construct was produced and tested using a luciferase assay. Results indicate that the rAAV-pir-miR34a construct efficiently downregulates expression of the reporter gene (e.g., luciferase) (FIG. 7B) in vitro. Analysis by qPCR demonstrates that miR34a overexpression inhibits growth of prostate cancer cells (FIG. 8A). In particular, it was found that overexpression of miR-34a significantly inhibits the cell cycle of PC3 cells (FIG. 8B) by prolonging $G_1$ (FIG. 8C-8D) and shortening S phases through targeting cyclin D1 (CCND1), CD44, and DNA topoisomerase 2-alpha (TOP2A), as shown in FIG. 8E. It was also observed that miR34a overexpression reduces cell viability (FIGS. 9A-9B) and inhibits cell migration of PC3 cells as measured by a wound healing assay (FIG. 9C-9D).

Figure 10A:
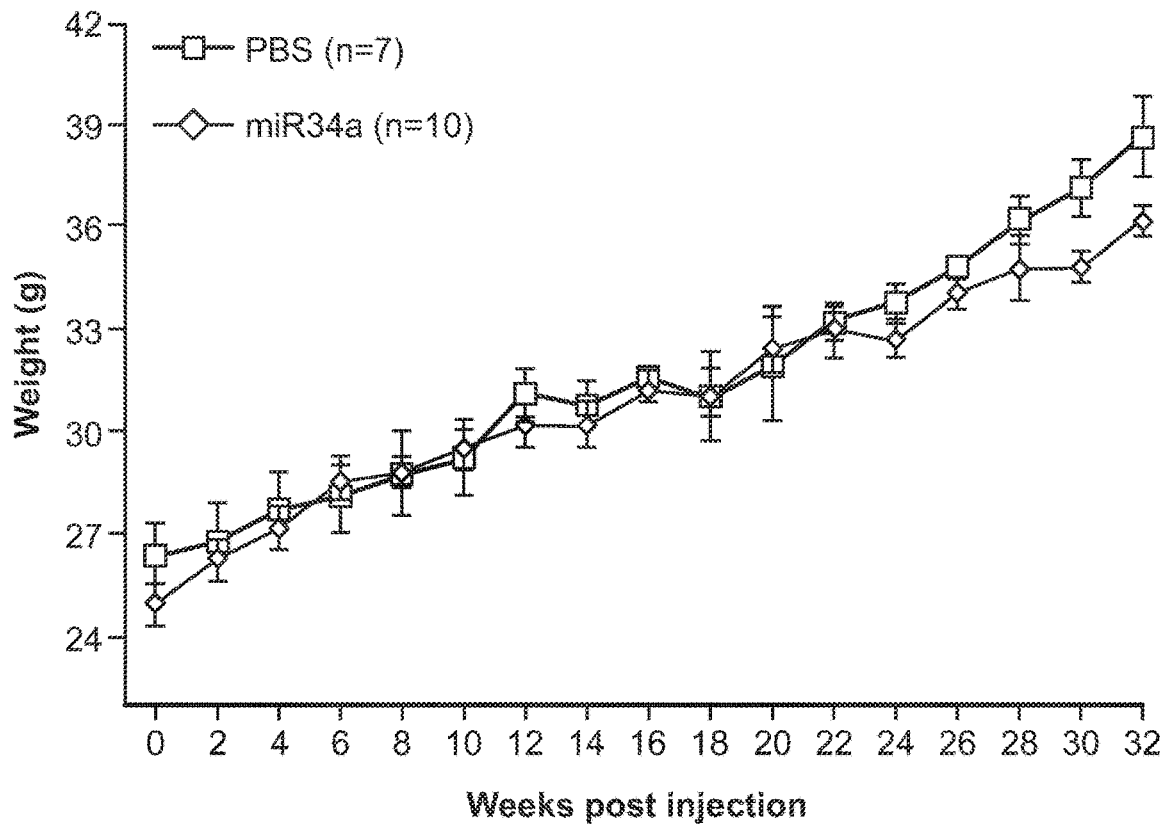
FIGS. 10A-10B show miR34a increases the survival rate of TRAMP mice.
Figure 10B:
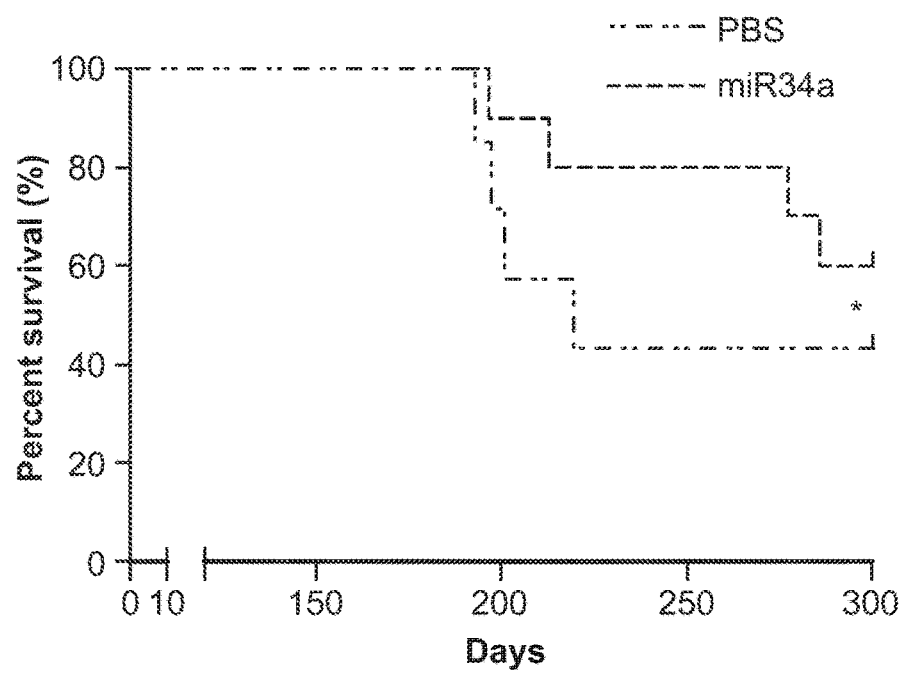
Figure 11:
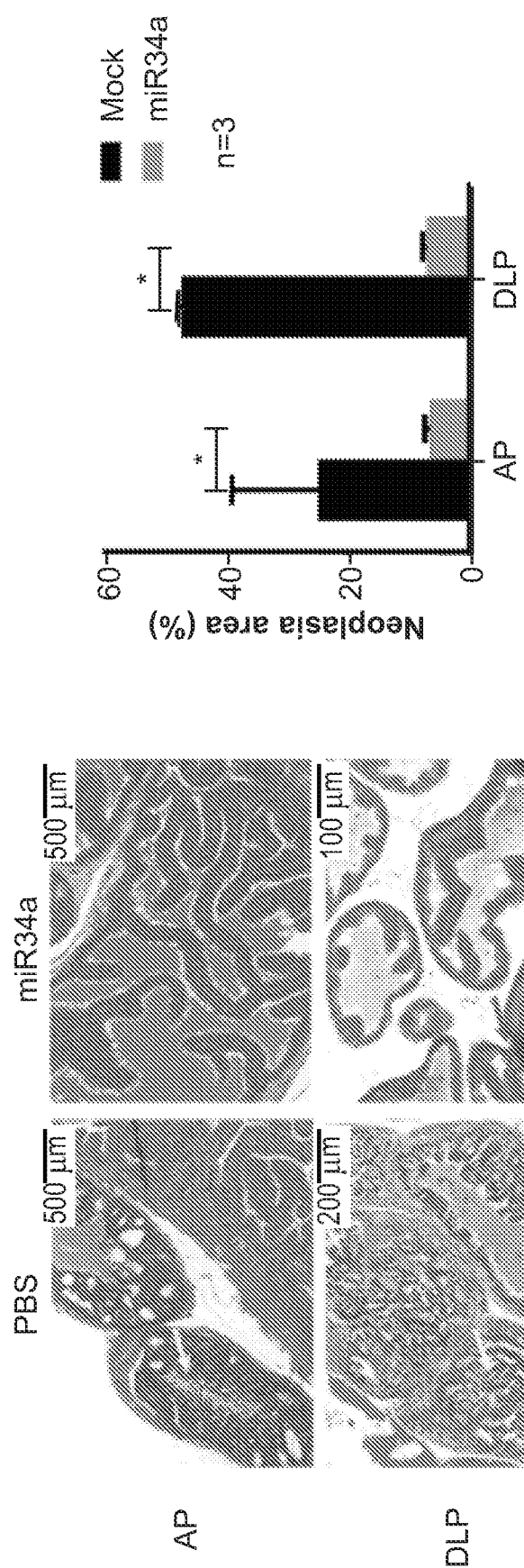
FIG. 11 shows miR34a overexpression ameliorates prostate cancer progression in vivo. 2-month old TRAMP mice were intraprostatically injected with rAAV7-miR34a ($4\times10^{11}$ GC/mouse). miR34a-treated mice show a decrease in prostate tissue pathology in both the anterior prostate (AP) and the dorsal lateral prostate (DLP) compared to PBS-injected control mice. Treatment with miR34a also results in significantly lower neoplasia area compared to control mice.

To investigate if in vivo gene delivery of pri-miR34a to the prostates of TRAMP mice can inhibit PCa progression, 12 serotypes of rAAVs were screened for efficient prostate targeting in vivo and in PCa cells in vitro. Several candidate vectors (e.g., AAV6.2, AAV7 and AAV9) were identified. Intraprostatic injection of rAAV9-pri-miR34a ($4 \times 10^{11}$ GCs/prostate) to 8-week old TRAMP mice for inhibition of PCa progression was investigated. Treatment with rAAV7-miR34a lowered body weights significantly ($p<0.05$) as compared to the control group starting from 24 weeks after injection, likely a result of the higher tumor burden in the control group (FIG. 10A). rAAV7-miR34a treatment also significantly extended the lifespan of TRAMP mice ($p<0.05$) (FIG. 10B). Moreover, proliferation and neoplasia in the rAAV7-mir34a treated prostates were significantly diminished in both the anterior prostate (AP) and dorsal lateral prostate (DLP) when compared to those in the control group (FIG. 11).

Figure 12A:
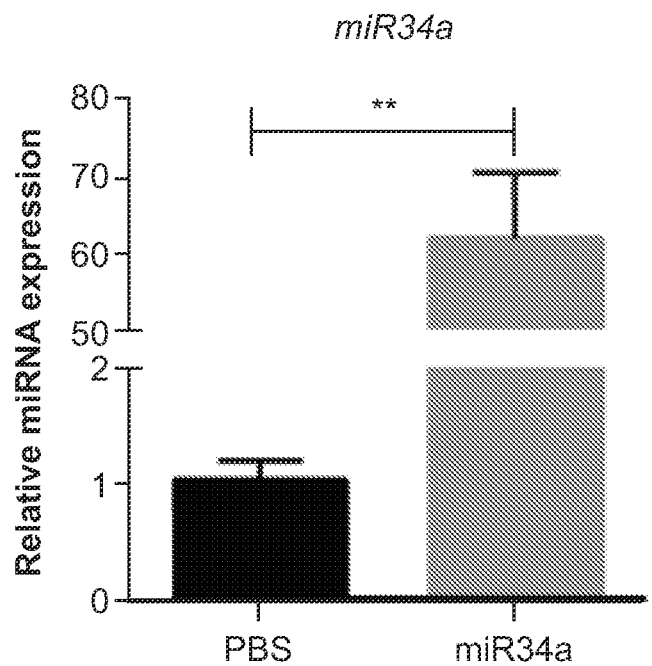
FIGS. 12A-12C show miRNA and target expression in mouse prostate 3 weeks post-intraprostatic injection ($4\times10^{11}$ GC/mouse).
Figure 12B:
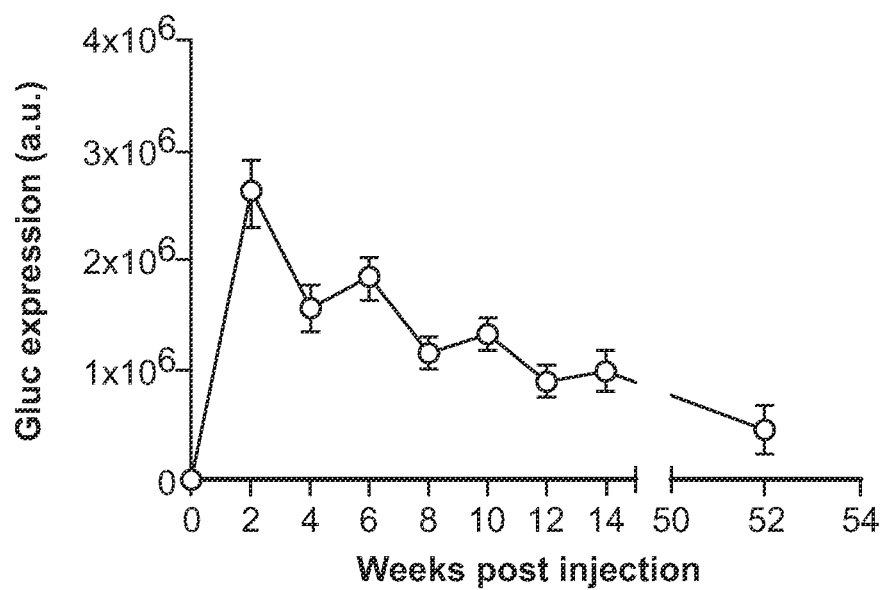
Figure 12C:
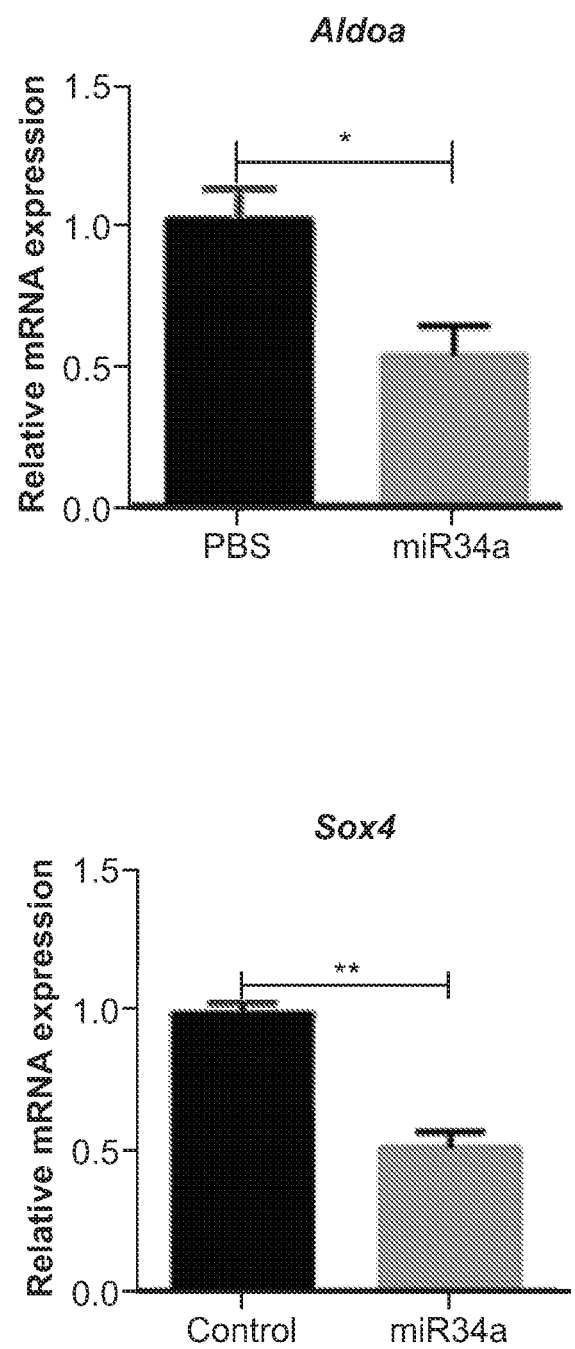
Figure 13:
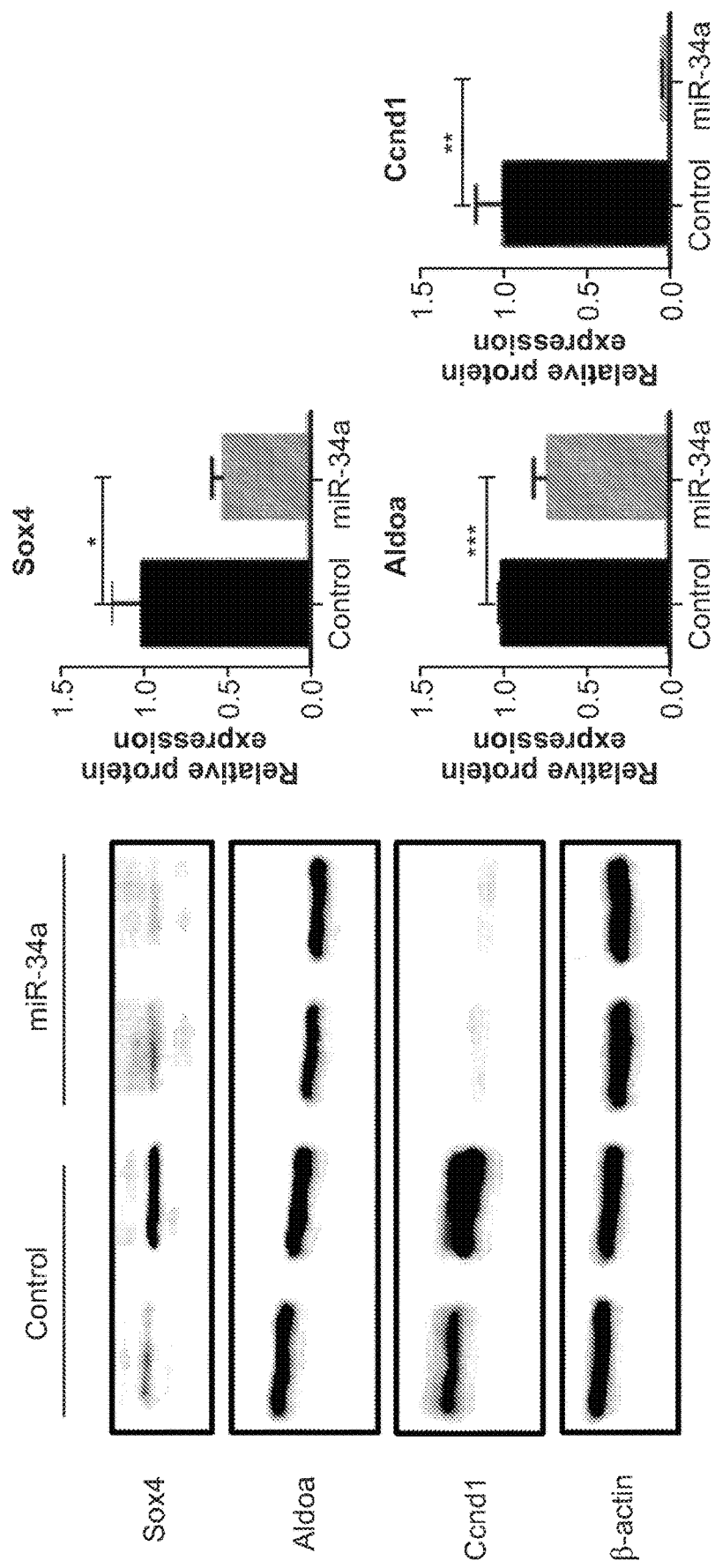
FIG. 13 shows Western blots demonstrating that miR34a overexpression downregulates Aldoa, Ccnd1, and Sox4 expression in mouse prostate compared to control mouse prostate.

Longevity of miR34a expression was also investigated. miRNA and reporter expression in mouse prostate were measured by qPCR and reporter (Gluc) assay 3 weeks post intraprostatic injection. Results indicate that miR34 expression is highly upregulated in treated mice versus control mice (FIG. 12A) and that miR34 expression persists for up to 52 weeks after injection (FIG. 12B). It was also observed that expression of Aldolase A, Fructose-Bisphosphate (AL-DOA) and Sex Determining Region Y)-Box 4 (Sox4) were significantly downregulated in miR34a-treated mouse prostate compared to untreated control mouse prostate (FIG. 12C). Relative protein expression results were confirmed by Western blot, which show miR34a overexpression downregulates ALDOA, Ccnd1, and Sox4 expression in mouse prostate (FIG. 13).

In sum, these results demonstrate the potential of rAAV-mediated efficient modulation of miRNA expression in the prostate for inhibiting PCa progression.

What is claimed is:

1. A method for delivering a transgene to prostate tissue, the method comprising:
administering to prostate tissue of a subject an effective amount of a recombinant adeno-associated virus (rAAV), wherein the rAAV comprises (i) a wild-type capsid protein comprising an amino acid sequence that is identical to any one of SEQ ID NO: 1 or 3-7, and (ii) an isolated nucleic acid comprising a promoter operably linked to a transgene, and wherein the rAAV infects cells of the prostate tissue.

2. The method of claim 1, wherein the capsid protein consists of an amino acid sequence that is identical to any one of SEQ ID NO: 1 or 3-7.

3. The method of claim 1, wherein the transgene encodes a gene associated with a prostate disease, optionally wherein the prostate disease is selected from prostatitis, prostate cancer, and benign prostate hyperplasia (BPH).

4. The method of claim 3, wherein the gene encodes a gene selected from the group consisting of B-cell lymphoma 2 (BCL-2), phosphatase and tensin homolog (PTEN), solute carrier family 39 member 1 (SLC39A1), breast cancer type 1 (BRCA1), breast cancer type 2 (BRCA2), hereditary prostate cancer-1 (HPC1), Runt-related transcription factor 2 (RUNX2), chloride channel accessory 2 (CLCA2), yes-associated protein 1 (YAP1), mammary serine protease inhibitor (MASPIN), LL37, cyclin dependent kinase inhibitor 1B (CDKN1B), androgen receptor (AR), NKX3.1, caspase 9 (CASP9), forkhead in rhabdomyosarcoma (FKHR), glycogen synthase kinase 3 (GSK3), mouse double minute 2 homolog (MDM2), extracellular signal-regulated kinase 1/2 (ERK1/2), prostate-specific antigen (PSA), cyclin D1 (CCND1), aldolase A (ALDOA), SRY-related HMG-box 4 (Sox4), CD44, and miR34a.

5. The method of claim 1, wherein the administration occurs by injection, optionally wherein:
i) the injection is not intraperitoneal (i.p.) injection; or
ii) the injection is intraprostate injection.

6. The method of claim 1, wherein the administration results in transduction of a prostate cell type selected from the group consisting of luminal prostate cells, basal prostate cells, and stromal prostate cells, optionally at least two prostate cell types.

7. The method of claim 1, wherein the rAAV further comprises two AAV inverted terminal repeats (ITRs), wherein the ITRs flank the transgene.

8. The method of claim 1, wherein the capsid protein consists of an amino acid sequence that is identical to any one of SEQ ID NO: 1 or 3-7.

9. The method of claim 1, wherein the capsid protein comprises an amino acid sequence that is identical to SEQ ID NO: 3 or 4.

10. A method for treating a prostate disease, the method comprising: administering to the prostate tissue of a subject having or suspected of having a prostate disease an effective amount of rAAV, wherein the rAAV comprises (i) a wild-type capsid protein comprising an amino acid sequence that is identical to any one of SEQ ID NO: 1 or 3-7, and (ii) an isolated nucleic acid comprising a promoter operably linked to a transgene, and wherein the rAAV infects cells of the prostate tissue.

11. The method of claim 10, wherein the capsid protein consists of an amino acid sequence that is identical to any one of SEQ ID NO: 1 or 3-7.

12. The method of claim 10, wherein the transgene encodes a gene associated with a prostate disease, optionally wherein the prostate disease is selected from prostatitis, prostate cancer, and benign prostate hyperplasia (BPH).

13. The method of claim 12, wherein the gene encodes a gene selected from the group consisting of B-cell lymphoma 2 (BCL-2), phosphatase and tensin homolog (PTEN), solute carrier family 39 member 1 (SLC39A1), breast cancer type 1 (BRCA1), breast cancer type 2 (BRCA2), hereditary prostate cancer-1 (HPC1), Runt-related transcription factor 2 (RUNX2), chloride channel accessory 2 (CLCA2), yes-associated protein 1 (YAP1), mammary serine protease inhibitor (MASPIN), LL37, cyclin dependent kinase inhibitor 1B (CDKN1B), androgen receptor (AR), NKX3.1, caspase 9 (CASP9), forkhead in rhabdomyosarcoma (FKHR), glycogen synthase kinase 3 (GSK3), mouse double minute 2 homolog (MDM2), extracellular signal-regulated kinase 1/2 (ERK1/2), prostate-specific antigen (PSA), cyclin D1 (CCND1), aldolase A (ALDO), SRY-related HMG-box 4 (Sox4), CD44, and miR34a.

14. The method of claim 10, wherein the administration occurs by injection, optionally wherein:
i) the injection is not intraperitoneal (i.p.); or
ii) the injection is intraprostate injection.

15. The method of claim 10, wherein the rAAV further comprises two AAV inverted terminal repeats (ITRs), wherein the ITRs flank the transgene.

16. The method of claim 10, wherein the capsid protein comprises an amino acid sequence that is identical to SEQ ID NO: 3 or 4.

17. A method for treating a prostate disease, the method comprising: administering to a subject having or suspected of having a prostate disease an effective amount of a recombinant adeno-associated virus (rAAV) comprising a wild-type capsid protein comprising an amino acid sequence that is identical to any one of SEQ ID NO: 1 or 3-7 and a promoter operably linked to a transgene, wherein the transgene encodes miR34a, and wherein the rAAV infects cells of prostate tissue.

18. The method of claim 17, wherein the transgene:
   i) comprises the sequence set forth in SEQ ID NO.: 15 or 16; or
   ii) is flanked by adeno-associated virus inverted terminal repeats (AAV ITRs).

19. The method of claim 17, wherein the administration occurs by injection, optionally wherein:
   i) the injection is not intraperitoneal (i.p.) injection; or
   ii) the injection is intraprostate injection.

20. The method of claim 17, wherein the capsid protein comprises an amino acid sequence that is identical to SEQ ID NO: 3 or 4.

* * * * *

UNITED STATES PATENT AND TRADEMARK OFFICE
CERTIFICATE OF CORRECTION

PATENT NO. : 11,426,469 B2
APPLICATION NO. : 15/769953
DATED : August 30, 2022
INVENTOR(S) : Guangping Gao et al.

It is certified that error appears in the above-identified patent and that said Letters Patent is hereby corrected as shown below:

In the Claims

In Claim 13, Column 80, Line 46, the text "(ALDO)" should read --(ALDOA)--

Signed and Sealed this
Eighteenth Day of October, 2022

Katherine Kelly Vidal
*Director of the United States Patent and Trademark Office*